United States Patent [19]

Erlich et al.

[11] Patent Number: 5,541,065
[45] Date of Patent: * Jul. 30, 1996

[54] METHOD FOR HLA DP TYPING

[75] Inventors: Henry A. Erlich, Oakland, Calif.; Glenn T. Horn, Framingham, Mass.; Teodorica Bugawan, San Leandro; Ann B. Begovich, El Cerrito, both of Calif.

[73] Assignee: Hoffmann-La Roche Inc., Nutley, N.J.

[*] Notice: The term of this patent shall not extend beyond the expiration date of Pat. No. 5,310,893.

[21] Appl. No.: 195,615

[22] Filed: Feb. 14, 1994

Related U.S. Application Data

[63] Continuation of Ser. No. 347,506, May 4, 1989, Pat. No. 5,310,893, which is a continuation-in-part of Ser. No. 258,212, Oct. 14, 1988, abandoned, which is a continuation-in-part of Ser. No. 196,660, May 20, 1988, abandoned, which is a continuation-in-part of Ser. No. 899,344, Aug. 22, 1986, abandoned, which is a continuation-in-part of Ser. No. 839,331, Mar. 13, 1986, abandoned.

[51] Int. Cl.⁶ .............................. C12Q 1/68; C07H 21/04
[52] U.S. Cl. .................... 435/6; 536/24.31; 536/24.33
[58] Field of Search ......................... 435/6; 536/24.31, 536/24.33

[56] References Cited

U.S. PATENT DOCUMENTS

| | | | |
|---|---|---|---|
| 2,683,202 | 7/1987 | Mullis | 435/91 |
| 4,582,788 | 4/1986 | Erlich | 435/6 |
| 4,683,195 | 7/1987 | Mullis et al. | 435/6 |
| 4,889,818 | 12/1989 | Gelfand et al. | 435/194 |
| 5,110,920 | 5/1992 | Erlich | 536/27 |

FOREIGN PATENT DOCUMENTS

| | | |
|---|---|---|
| 0237362 | 9/1987 | European Pat. Off. |
| 8904875 | 6/1989 | WIPO |

OTHER PUBLICATIONS

Wank et al., 1978, "The Lymphocyte Restimulation System: Evaluation by Intra-HLA-D Group Priming" Immunogenetics 6:107–115.

Mawas et al., 1980, "Split of HLA-D into Two Regions Alpha and Beta by a Recombination Between HLA-D and GLO. I. Study in a Family and Primed Lymphocyte Typing for Determinants Coded by the Beta Region" Tissue Antigens 15:458–466.

Shaw et al., 1980, "Evidence for a New Segregant Series of B-Cell Antigens that are Encoded in the HLA-D Region and that Stimulate Secondary Allogeneic Proliferative and Cytotoxic Responses" J. Experimental Medicine 152:565–580.

Kavathas et al., Oct., 1981, "SB: A New HLA-Linked Human Histocompatibility Gene Defined Using HLA-Mutant Cell Lines" Nature 293:747–749.

Shaw et al., 1982, "Serologic Identification of the Human Secondary B Cell Antigens" J. Experimental Medicine 156:731–743.

Wake et al., Nov., 1992, "Allelic Polymorphism and Complexity of the Genes for HLA-DR B-Chains-Direct Analysis by DNA-DNA Hybridization" Nature 300:372–374.

Bohme et al., Jan., 1983, "Human Class II Major Histocompatibility Antigen B-Chains are Derived From at Least Three Loci" Nature 301:82–84.

Choi et al., Jul., 1983, "Murine I-AB Chain Polymorphism: Nucleotide Sequences of Three Allelic I-AB Genes" Science 221:283–286.

Roux-Dosseto et al., "Genetic Mapping of a Human Class II Antigen B-Chain cDNA Clone to the SB Region of the HLA Complex" Proc. Natl. Acad. Sci. USA 80:6036–6040.

Kappes et al., 1984, "Structure and Polymorphism of the HIA Class II SB Light Chain Genes" The EMBO Journal 3(12):2985–2993.

Gorski et al., Jul., 1984, "Molecular Organization of the HLA-SB Region of the Human Major Histocompatibility Complex and Evidence for Two SB B-Chain Genes" Proc. Natl. Acad. Sci. USA 81:3934–3938.

Gutafsson et al., May, 1984, "Isolation of a cDNA Clone Coding for an SB B-Chain" Nature 309:76–78.

Servenius et al., 1984, "Molecular Map of the Human HLA-SB (HLA-DP) Region and Sequence of an SBalpha (DPalpha) Pseudogene" The EMBO Journal 3(13):3209–3214.

Spielman et al., Jun., 1984, "Six HLA-D Region Alpha-Chain Genes on Human Chromosome 6: Polymorphisms and Associations of DC Alpha-Related Sequences With DR Types" Proc. Natl. Acad. Sci. USA 81:3461–3465.

Giles and Capra, 1985, "Structure, Function, and Genetics of Human Class II Molecules" Advances Immunology 37:1–71.

(List continued on next page.)

Primary Examiner—George C. Elliott
Assistant Examiner—John S. Brusca
Attorney, Agent, or Firm—George M. Gould; Stacey R. Sias; Douglas A. Petry

[57] ABSTRACT

A process for determining the genotype of an individual with respect to the alleles at the HLA DP locus involves obtaining a sample of nucleic acid from the individual, and hybridizing the nucleic acids with a panel of probes specific for variant segments of DPalpha and DPbeta genes. Because the variation between DPbeta alleles is highly dispersed throughout the second exon of the DPbeta gene, the discovery of many different DPbeta alleles makes the process far more discriminating and informative than cellular, RFLP, or serological methods. The process can also be carried out on amplified nucleic acid produced by the polymerase chain reaction using primers specific for the second exon of the DPalpha and DPbeta genes. HLA DP DNA typing methods are useful in the prevention of graft rejection and host versus graft disease, in determining susceptibility to autoimmune diseases, in providing evidence concerning the derivation from an individual of forensic samples, and in paternity testing.

12 Claims, No Drawings

OTHER PUBLICATIONS

Kelly and Trowsdale, Nov., 1985, "Complete Nucleotide Sequence of a Functional HLA–DPBeta Gene and the Region Between the DPBeta1 and DPalpha1 Genes: Comparison of the 5' Ends of HLA Class II Gene" Nucleic Acids Research 13(5):1607–1621.

Trowsdale et al., 1985, "Structure, Sequence and Polymorphism in the HLA–D Region" Immunological Reviews 85:5–43.

Ando et al., 1986, "Isolation and Allelic Polymorphism of cDNA Clones and Genomic Clones of HLA–DP Heavy and Light Chains" Human Immunology 17:355–367.

Hoffman et al., 1986, "HLA–DP Antigens in Patients With Pauciarticular Juvenile Rheumatoid Arthritis" Arthritis and Rheumatisim 29(9):1057–1062.

Odum et al., 1986, "Increased Frequency of HLA–DPw2 in Pauciarticular Onset Juvenile Chronic Arthritis" Tissue Antigens 28:245–250.

Saiki et al., Nov., 1986, "Analysis of Enzymatically Amplified B–Globin and HLA–DQalpha DNA With Allele–Specific Oligonucleotide Probes" Nature 324(13):163–166.

Scharf et al., 1986, "Direct Cloning and Sequence Analysis of Enzymatically Amplified Genomic Sequences" Science 233:1076–1078.

Silver and Goyert, HLA Class II Antigens, Springer–Verlag, 1986, pp. 32–48 entitled "Epitopes are the Functional Units of HLA Class II Molecules and Form the Molecular Basis for Disease Susceptibility".

Amar et al., Mar. 1987, "HLA–DP and HLA–DO Genes in Presumptive HLA–Identical Siblings: Structural and Functional Indentification of Allelic Variation" J. Immunology 138(6):1947–1953.

Bodmer et al., Jul., 1987, "Identification of HLA–DP Polymorphism With DPalpha and DPbeta Probes and Monoclonal Antibodies: Correlation With Primed Lymphocyte Typing" Proc. Natl. Acad. Sci. USA 84:4596–4600.

Gustafsson et al., Jun., 1987, "Class II Genes of the Human Major Histocompatibility Complex" J. Biological Chemistry 262(8):8778–8786.

Hyldig–Nielsen et al., Mar., 1987, "Restriction Fragment Length Polymorphism of the HLA–DP Subregion and Correlations to HLA–DP Phenotypes" Proc. Natl. Acad. Sci. USA 84:1644–1648.

Lotteau et al., 1987, "Biochemical Polymorphism of the HLA–DP Heavy Chain" Immunogenetics 25:403–407.

Odum et al., 1987, "A 'New' Supertypic HLA–DP Related Determinant Detected by Primed Lymphocyte Typing (PLT)" Tissue Antigens 29:101–109.

Begovich et al., 1988, "The Use of the Polymerase Chain Reaction to Analyze HLA Class II Sequence Polymorphism and Genetic Sysceptibility to Myasthenia Gravis" 23(2):81.

Bugawan et al., 1988, "The Use of Non–Radioactive Oligonucleotide Probes to Analyze Enzymatically Amplified DNA for Prenatal Diagnosis and Forensic HLA Typing" Bio/Technology 6:943–947.

Bugawan et al., 1988, "Analysis of HLA–DP Allelic Sequence Polymorphism Using the in Vitro Enzymatic NDA Amplification of DP–alpha and DP–beta Loci" J. Immunology 141(12):4024–4030.

Compagnone–Post, 1988, "The Beta–Chains of DP4 Molecules From Different Haplotypes are Encoded by the Same Gene" Genomics 2:8–13.

Horn et al., Aug. 1988, "Allelic Sequence Variation of the HLA–DQ Loci: Relationship to Serology and to Insulin–Dependent Diabetes Susceptibility" Proc. Natl. Acad. Sci. USA 85:6012–6016.

Howell et al., Jan., 1988, "An Extended HLA–D Region Haplotype Associated With Celiac Disease" Proc. Natl. Acad. Sci. USA 85:222–226.

Kappes and Strominger, 1988, "Human Class II Major Histocompatibility Complex Genes and Proteins" Ann. Rev. Biochem. 57:991–1028.

Maeda et al., 1988, "HLA–DP Typing by Analysis of DNA Restriction Fragment Length Polymorphisms in the HLA–DPbeta Subregion" 3–Biochem. Genetics 109:1782 (Abstract No. 1766k).

Maeda et al., 1988, "HLA–DP Typing by Analysis of DNA Restriction Fragment Length Polymorphisms in the HLA–DPbeta Subregion" Human Immunology 21:239–248.

Odum et al., 1988, "HLA–DP Antigens are Involved in the Susceptibility to Multiple Sclerosis" Tissue Antigens 31:235–237.

Scharf et al., 1988, "New Methodology for HLA Class II Oligonucleotide Typing Using Polymerase Chain Reaction" Human Immunology 23(2):143.

Scharf et al., May, 1988, "HLA Class II Allelic Variation and Susceptibility to Pemphigus Vulgaris" Proc. Natl. Acad. Sci. USA 85:3504–3508.

Angelini et al., 1989, "HLA–DP Typing by DNA Amplification and Hybridization With Specific Oligonucleotides" Human Immunology 26:169–177.

Begovich et al., Dec., 1989, "A Specific HLA–DPbeta Allele is Associated With Pauciarticular Juvenile Rheumatoid Arthritis but not Adult Rheumatoid Arthritis" Proc. Natl. Acad. Sci. USA 86:9489–9493.

Bugawan et al., Jun. 1989, "A Combination of a Particular HLA–DPbeta Allele and an HLA–DQ Heterodimer Confers Susceptibility to Coeliac Disease" Nature 339:470–473.

Lee et al., 1989, "Sequence Polymorphism of HLA–DP Beta Chains" Immunogenetics 29:346–349.

METHOD FOR HLA DP TYPING

CROSS-REFERENCE TO RELATED APPLICATIONS

This application is a continuation of application Ser. No. 07/347,506, filed May 4, 1989, now U.S. Pat. No. 5,310,893, which is a continuation-in-part (CIP) of now abandoned U.S. Ser. No. 258,212, filed Oct. 14, 1988, which is a CIP of Ser. No. 196,660, filed May 20, 1988, now abandoned, which is a CIP of Ser. No. 899,344, filed Aug. 22, 1986 now abandoned, which in turn is a CIP of Ser. No. 839,311 filed Mar. 13, 1986, now abandoned. The disclosures of all of the above-referenced patents and applications are incorporated herein by reference.

BACKGROUND OF THE INVENTION

1. Field of the Invention

This invention relates to a method and compositions for determining the HLA DP genotype of an individual. In a preferred embodiment, the invention relates to using gene amplification methodology disclosed and claimed in U.S. Pat. Nos. 4,683,195 and 4,683,202 and the dot-blot and allele-specific oligonucleotide probe technology as disclosed and claimed in U.S. Pat. No. 4,683,194. The methods and probes of the invention specifically relate to the detection of the polymorphic class II HLA DP genes. The invention relates to the fields of molecular biology, diagnostic medicine, and forensics.

2. Description of the Related Art

The class II loci of the human major histocompatibility complex encode the HLA D cell surface glycoproteins which are expressed on B lymphocytes, activated T lymphocytes, macrophages, and dendritic cells. These proteins, which are individually designated DR, DQ, and DP, are composed of an alpha and a highly polymorphic beta subunit and are responsible for the presentation of antigen to T cells. The variability in the highly polymorphic beta subunit is localized to the amino-terminal extracellular domain, which is thought to interact with the T cell receptor and antigen peptide fragments. The genes encoding the class II HLA proteins are located on the short arm of chromosome six in humans. The genes encoding the HLA DPalpha and DPbeta chains are clustered at the centromeric end of this region and, perhaps due to low levels of expression, were the last of the HLA D genes to be discovered and are, therefore, the least well characterized. The structures, sequences, and polymorphisms in the HLA D region have been reviewed in Trowsdale et al., 1985, *Immunol. Rev.* 85:5–43, incorporated herein by reference.

The polymorphism of the HLA D region gene products has, in general, been defined by serologic typing reagents and by the mixed lymphocyte culture (MLC) reaction in which T cell proliferation in response to homozygous typing cells (HTC) is measured in culture. The HLA DP antigens were originally defined by their ability to stimulate a strong secondary response in specifically primed T cells, a method known as primed lymphocyte typing (PLT) and described by Mawas et al., 1981, *Tissue Antigens* 15:458–466; Wank et al., 1978, *Immunogenetics* 6:107–115;and Shaw et al., 1980, *J. Exp. Med.* 152:565–580. The HLA DP antigens elicit only a weak response in a primary MLC, and unlike the studies of HLA DR and HLA DQ polymorphism, the analysis of allelic variation in the HLA DP region has been complicated by the lack of availability of serologic reagents and of typing cells. In addition, the specific cell lines used in the PLT assay are difficult to generate, and the typing assay is slow and somewhat variable from laboratory to laboratory.

Cellular (see Odum et al., 1987, *Tissue Antigens* 29:101–109), biochemical (see Lotteau et al., 1987, *Immunogenetics* 25:403–407), and restriction fragment length polymorphism (RFLP, see Hyldig-Nielsen et al., 1987, *Proc. Natl. Acad. Sci. U.S.A.* 84:1644–1648) analyses have indicated that the degree of polymorphism in the DP region may be more extensive than the currently serologically, immunologically, or PLT-defined DPw1 through DPw6 types. The RFLP approach showed that the RFLP of the DP region was relatively extensive and that some of the fragments were strongly associated with certain DP antigens. However, the RFLP technique has certain limitations. An allele carrying a variant sequence is identifiable only if the variant nucleotide is within the recognition site of a restriction enzyme used in the analysis or if a polymorphic restriction site is in linkage disequilibrium with a specific coding sequence variation. In addition, RFLP analysis simply provides evidence that a coding sequence variation exists but does not provide information on the exact nature of the variation. Moreover, relatively large fragments of the genomic nucleic acid must be used for the analysis. This latter requirement often rules out the use of samples which have been kept under conditions which result in the degradation of the genomic DNA.

Accurate DP typing may prove important in several medical applications. Genetic recombination between the DP loci and the serologically typed DR loci can occur such that serologically identical sibs may not be matched at DP. The HLA-DP differences have been revealed by RFLP analysis in several cases of acute graft vs. host disease between apparently HLA-identical donor and recipient pairs, as described by Amar et al., 1987, *J. Immunology* 138: 1947–1953. Furthermore, several autoimmune diseases, including coeliac disease, have been shown to be associated with specific DP types, defined either by PLT, Odum et al., 1986, *Tissue Antigens* 28:245–250, or by RFLP, Howell et al., 1988, *Proc. Natl. Acad. Sci. U.S.A.* 85:222–226, analysis.

A significant improvement in DNA amplification, the polymerase chain reaction (PCR) technique, was disclosed by Mullis in U.S. Pat. No. 4,683,202, and methods for utilizing PCR in the cloning and detection of nucleic acids were disclosed by Mullis et al. in U.S. Pat. No. 4,683,195, both of which patent disclosures are hereby incorporated herein by reference. See also U.S. Pat. No. 4,965,188 and abandoned U.S. Ser. No. 899,513, filed Aug. 22, 1986, each of which is incorporated herein by reference. In the PCR technique, short oligonucleotide primers are prepared to match opposite ends of the sequence to be amplified. The sequence between the primers need not be known. A sample of nucleic acid (DNA or RNA, although RNA is first convened to cDNA in the PCR process) is extracted and denatured, preferably by heat, and hybridized with oligonucleotide primers which are present in molar excess. Polymerization is catalyzed by a polymerase in the presence of deoxynucleoside triphosphates (dNTPs). This results in two "long products" which contain the respective primers at their 5'-termini, covalently linked to the newly synthesized complements of the original strands. The replicated DNA is again denatured, hybridized with oligonucleotide primers, returned to polymerizing conditions, and a second cycle of replication is initiated. The second cycle provides the two original strands, the two long products from cycle 1 and two long products of cycle 2, and two "short products" replicated from the long products produced in cycle 1. The short products contain sequences (sense or antisense) derived from the target sequence and flanked at the 5' end with a primer and at the 3'-end with a sequence complementary to a primer. On each additional cycle, the number of short products is replicated exponentially. Thus, the PCR process causes the amplification of a specific target sequence and allows for the detection of sequences initially present in a sample in only extremely small amounts.

Allelic sequence variations in the gene encoding beta-globin of hemoglobin and in the gene encoding HLA DQalpha have been detected by utilizing allele-specific oligonucleotides (ASO), which will only anneal to sequences that match them perfectly, as described by Saiki et al., 1986, *Nature* 324:163–166. These studies also utilized the PCR procedure to amplify the DNA sequences present in the samples and a dot-blot technique to detect probe hybridization to the sample.

SUMMARY OF THE INVENTION

The present invention solves the above listed problems in HLA DP typing and provides a relatively rapid, convenient, practical, accurate, and reproducible method for determining HLA DP genotypes. The method is based in pan upon the finding that there are a large number of previously unreported DPbeta alleles. The variation between alleles is of a highly dispersed nature. The present invention also provides nucleic acid probes for the regions of the HLA DPbeta gene that are most informative in discriminating between different DP alleles for use in the method.

These oligonucleotide probes are called SSOs (sequence specific oligonucleotides), which, under the appropriate conditions, are able to bind specifically to their complementary sequences. If a particular probe can be used to identify uniquely an allele, the probe is called an allele specific oligonucleotide (ASO). Because of the dispersed nature of the variation between the DPbeta alleles, rarely is any one probe able to identify uniquely a specific DPbeta allele. Rather, according to the methods of the present invention, the identity of an allele is inferred from the pattern of binding of a panel of probes, with each individual probe of the panel specific for different segments of the HLA DP gene. The probes comprise a nucleotide sequence totally complementary to a variant sequence of a variable segment of a DP gene. The complementary sequence of the probes is usually from 10 to 30 nucleotides in length, most often 17 to 19 nucleotides in length.

As noted above, PCR is quite an important tool in nucleic acid based diagnostic methods. The novel probes of the invention can of course be used to detect specific sequences in PCR-amplified DNA. To enable practice of PCR-based, HLA DP DNA typing, the present invention provides oligonucleotide primers that allow for the amplification of informative DP regions via PCR.

Accordingly, one aspect of the invention is a process for determining an individual's HLA DP genotype from a nucleic acid containing sample obtained from the individual comprising: (a) amplifying a target region of said nucleic acid which contains a polymorphic region of an HLA DP gene; (b) hybridizing the amplified nucleic acid with a panel of sequence specific oligonucleotide (SSO) probes specific for variant segments of HLA DP genes under conditions that allow said SSO probes and amplified nucleic acids to form stable hybrid duplexes; and (c) detecting hybrids formed between the amplified nucleic acids and the SSO probes.

Another aspect of the invention relates to kits useful for determining the HLA DP genotype of an individual; these kits comprise a panel of SSO probes for allelic variant sequences in said target region; and (b) instructions for determining the genotype by utilizing kit ingredients.

To aid in understanding the invention, several terms are defined below.

"Genotype" refers to a description of the genotypic variants of an allele present in an individual (or sample). The genotype of an individual may be determined, for example, by the use of serologic reagents, by the use of typing cells, by RFLP analysis of the genome, and, as discussed below, by the use of SSOs.

"HLA DP region" or "DP" refers to that region of the HLA D complex, described in Trowsdale et al., supra, which lies on the centromeric side of the HLA D region and contains two alpha and two beta genes, one pair of which are pseudogenes.

"Oligonucleotide" refers to primers, probes, nucleic acid fragments to be detected, nucleic acid controls, and unlabeled blocking oligomers and is defined as a molecule comprised of two or more deoxyribonucleotides or ribonucleotides. The exact size of an oligonucleotide will depend upon many factors and the ultimate function or use of the oligonucleotide. Oligonucleotides can be prepared by any suitable method. Such methods include, for example, cloning and restriction of appropriate sequences and direct chemical synthesis by a method such as the phosphotriester method of Narang et al., 1979, *Meth. Enzymol.* 68:90; the phosphodiester method of Brown et al., 1979, *Meth. Enzymol.* 68: 109; the diethylphosphoramidite method of Beaucage et al., 1981, *Tetrahedron Lett.* 22:1859–1862; and the solid support method in U.S. Pat. No. 4,458,066.

"Polymorphic" or "DNA polymorphism" refers to the condition in which two or more variations of a specific DNA sequence coexist in the same interbreeding population.

"Primer" refers to an oligonucleotide, whether natural or synthetic, capable of acting as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer is preferably an oligodeoxyribonucleotide and is single stranded for maximum efficiency in amplification, but may also be double stranded. If double stranded, the primer is first treated to separate its strands before being used to prepare extension products. The exact length of a primer will depend on many factors, but typically ranges from 15 to 25 nucleotides. Short primer molecules generally require cooler temperatures to form sufficiently stable hybrid complexes with the template. A primer need not reflect the exact sequence of the template but must be sufficiently complementary to hybridize with a template. An example of a non-complementary sequence which may be incorporated into the primer is a sequence which encodes a restriction enzyme recognition site (see U.S. Pat. No. 4,800,159).

"Primer," as used herein, may refer to more than one primer, particularly in the case where there is some ambiguity in the information regarding one or both ends of the target region to be amplified. For instance, if a nucleic acid sequence is inferred from a protein sequence, a "primer" is actually a collection of primer oligonucleotides containing sequences representing all possible codon variations based on the degeneracy of the genetic code. One of the primer oligonucleotides in this collection will be homologous with the end of the target sequence. Likewise, if a "conserved"

region shows significant levels of polymorphism in a population, mixtures of primers can be prepared that will amplify adjacent sequences. A primer can be labeled, if desired, by incorporating a label detectable by spectroscopic, photochemical, biochemical, immunochemical, or chemical means. For example; useful labels include $^{32}$p, fluorescent dyes, electron-dense reagents, enzymes (as commonly used in ELISAS), biotin, or haptens or proteins for which antisera or monoclonal antibodies are available. A labels can also be used to "capture" the primer, so as to facilitate the immobilization of either the primer or amplified DNA on a solid support.

"Restriction endonucleases" and "restriction enzymes" refer to enzymes, usually of bacterial origin, that cut double-stranded DNA at or near a specific nucleotide sequence.

"Restriction fragment length polymorphism" or "RFLP" refers to the differences in DNA nucleotide sequences that are randomly distributed throughout the entire genome and that produce different restriction endonuclease patterns for different individuals upon digestion of genomic DNA.

"Sequence-specific oligonucleotide" or "SSO" refers to oligonucleotides that have an exactly complementary sequence to the sequence to be detected, typically sequences characteristic of a particular DP allele, which under sequence-specific hybridization conditions will hybridize only to that exact complementary target sequence. The hybridization is under stringent conditions. Stringent hybridization conditions are known in the art, and are described, for example, in Maniatis et al., *Molecular Cloning: A Laboratory Manual* (New York, Cold Spring Harbor Laboratory, 1982). Depending on the sequences being analyzed, one or more sequence-specific oligonucleotides may be employed for each sequence. The terms "probe" and "SSO probe" are used interchangeably with SSO.

"Target region" refers to a region of a nucleic acid which is to be analyzed, which usually contains polymorphic DNA sequences.

"Thermostable polymerase enzyme" refers to an enzyme which is relatively stable to heat and which catalyzes the polymerization of nucleotides to form primer extension products that are complementary to one of the nucleic acid strands of the target sequence. Generally, the enzyme will initiate synthesis at the 3'-end of the target sequence utilizing the primer and will proceed in the 5'-direction along the template until synthesis terminates. A purified thermostable polymerase enzyme is described more fully in European Pat. Office (EPO) Publication 258,017; abandoned U.S. Ser. No. 143,441, filed Jan. 12, 1988; U.S. Pat. No. 4,889,818; and abandoned U.S. Ser. No. 899,241, filed Aug. 22, 1986, each of which is, incorporated herein by reference, and is commercially available from Perkin-Elmer Cetus Instruments.

DETAILED DESCRIPTION OF THE INVENTION

The present invention provides processes and reagents for determining the HLA DP genotype of an individual. In part, the invention results from the discovery of polymorphisms in the variable second exon of the HLA DPbeta genes by the combined methods of PCR amplification, cloning, and DNA sequencing. As a result, 22 DPbeta (DPB) allelic variants have been discovered. Based upon the novel sequence of these DP genes, SSO probes are provided for the detection of the variant genotypes. The variations between the different DP alleles are dispersed. Therefore, one probe alone is rarely able to identify uniquely a specific DPbeta allele. Rather, the identity of an allele is inferred from the pattern of binding of a panel of probes, with each individual probe of the panel specific to different segments of a DP gene.

In a preferred embodiment of the invention, the process for DNA based typing of HLA DP genotypes is comprised of amplifying a nucleic acid sequence which contains a variable portion of an HLA DP gene, determining the variant HLA DP sequence present using SSO probes; and inferring the HLA DP genotype from the pattern of binding of the SSO probes to the amplified target sequence. To facilitate practice of this preferred embodiment, the present invention provides primers useful in amplifying by PCR the HLA DP target region.

In this preferred method, a sample containing nucleic acid is obtained from an individual whose HLA DP genotype is to be determined. Any type of tissue containing HLA DP nucleic acid may be used for purposes of the present invention. Because the present invention also is compatible with amplified nucleic acids, and because the PCR technique can amplify extremely small quantities of nucleic acid, samples containing vanishingly small amounts of nucleic acid can be typed for the presence of particular HLA DP variants by the method of the present invention. For instance, even a single hair, contains enough DNA for purposes of the present invention, as evidenced by the work with DQalpha described by Higuchi et al., 1988, *Nature* 332:543–546.

In general, the nucleic acid in the sample will be DNA, most usually genomic DNA. However, the present invention can also be practiced with other nucleic acids, such as messenger RNA or cloned DNA, and the nucleic acid may be either single-stranded or double-stranded in the sample and still be suitable for purposes of the present invention. Those of skill in the art recognize that whatever the nature of the nucleic acid, the nucleic acid can be typed by the present method merely by taking appropriate steps at the relevant stage of the process. If PCR is used to amplify the nucleic acid in the sample, then the sample will usually comprise double-stranded DNA when typed with the novel probes of the invention.

As noted above, in a preferred embodiment, the HLA DP typing method and probes of the invention are used in conjunction with PCR-amplified target DNA. Those practicing the present invention should note, however, that amplification of HLA DP target sequences in a sample may be accomplished by any known method which provides sufficient amplification so that the target sequence may be detected by nucleic acid hybridization to an SSO probe. Although the PCR process is well known in the art (see U.S. Pat. Nos. 4,683,195 and 4,683,202) and although a variety of commercial vendors, such as Perkin-Elmer/Cetus instruments, sell PCR reagents and publish PCR protocols, some general PCR information is provided below for purposes of clarity and full understanding of the invention to those unfamiliar with the PCR process.

To amplify a target nucleic acid sequence in a sample by PCR, the sequence must be accessible to the components of the amplification system. In general, this accessibility is ensured by isolating the nucleic acids from the sample. A variety of techniques for extracting nucleic acids from biological samples are known in the art. For example, see those described in Maniatis et al., *Molecular Cloning: A Laboratory Manual*, (New York, Cold Spring Harbor Laboratory, 1982). Alternatively, if the sample is fairly readily disruptable, the nucleic acid need not be purified prior to amplification by the PCR technique, i.e., if the sample is comprised of cells, particularly peripheral blood lymphocytes or amniocytes, lysis and dispersion of the intracellular components may be accomplished merely by suspending the cells in hypotonic buffer.

Because the nucleic acid in the sample is first denatured (assuming the sample nucleic acid is double-stranded) to begin the PCR process, and because simply heating some samples results in the disruption of cells, isolation of nucleic acid from the sample can sometimes be accomplished in conjunction with strand separation. Strand separation can be accomplished by any suitable denaturing method, however, including physical, chemical, or enzymatic means. Typical heat denaturation involves temperatures ranging from about 80° C. to 105° C. for times ranging from about 1 to 10 minutes. Strand separation may also be induced by a helicase, an enzyme capable of exhibiting helicase activity. For example, the enzyme RecA has helicase activity in the presence of ATP. The reaction conditions suitable for strand separation by helicases are known in the art (see Kuhn Hoffman-Berling, 1978, *CSH-Quantitative Biology* 43:63 and Radding, 1982, *Ann. Rev. Genetics.* 16:405–436).

As noted above strand separation may be accomplished in conjuction with the isolation of the sample nucleic acid or as a separate step. In addition, strand separation can be achieved simultaneously with the next step in the PCR process: annealing of primers and synthesis of primer extension products. In this embodiment of the PCR process, the temperature is very carefully controlled so that strand separation and primer annealing and extension occur in equilibrium. In this embodiment of the PCR process, the reaction is catalyzed by a heat-stable polymerase and carried out at an elevated temperature. The temperature is one at which the enzyme is thermostable, and at which the nucleic acids are in an equilibrium of single and double strands, so that sufficient primer will anneal to template strands to allow a reasonable rate of polymerization. In the preferred embodiment of the PCR process, however, strand separation is achieved by heating the reaction to a sufficiently high temperature for an effective time to cause the denaturation of the duplex, but not to cause an irreversible denaturation of the polymerase (see EP No. 258,017).

No matter how strand separation is achieved, however, once the strands are separated, the next step in PCR involves hybridizing the separated strands with primers that flank the target sequence. The primers are then extended to form complementary copies of the target strands, and the cycle of denaturation, hybridization, and extension is repeated as many times as necessary to obtain the desired amount of amplified nucleic acid.

As noted above, the present invention provides PCR primers for HLA DP DNA amplification and typing. These primers are complementary to sequences in the conserved regions that flank the target sequences in the variant regions of the HLA DP loci. For purposes of the present invention, the preferred variant region of the HLA DP loci is the second exon of the DPalpha and DPbeta genes. For successful PCR amplification, the present primers are designed so that the position at which each primer hybridizes along a duplex sequence is such that an extension product synthesized from one primer, when it is separated from its template (complement), serves as a template for the extension of the other primer to yield an amplified segment of nucleic acid of defined length. Moreover, primers are provided that will bind preferentially to the HLA-DP region under selective annealing conditions.

Template-dependent extension of primers in PCR is catalyzed by a polymerizing agent in the presence of adequate amounts of four deoxyribonucleoside triphosphates (dATP, dGTP, dCTP, and dTTP) in a reaction medium comprised of the appropriate salts, metal cations, and pH buffering system. Suitable polymerizing agents are enzymes known to catalyze template-dependent DNA synthesis. For example, if the template is RNA, a suitable polymerizing agent to convert the RNA into a complementary DNA (cDNA) sequence is reverse transcriptase (RT), such as avian myeloblastosis virus RT. Once the target for amplification is DNA, suitable polymerases include, for example, *E. coli* DNA polymerase I or its Klenow fragment, $T_4$ DNA polymerase, and Taq polymerase, a heat stable DNA polymerase isolated from *Thermus aquaticus* and commercially available from Perkin-Elmer/Cetus Instruments (PECI). The latter enzyme is widely used in the amplification and sequencing of nucleic acids. The reaction conditions for using DNA polymerases are known in the art, and are described in, for example, the treatise *Methods in Enzymology*, and in Maniatis et al., *Molecular Cloning: A Laboratory Manual, supra.*

The PCR method can be performed in a step-wise fashion, where after each step new reagents are added, or in a fashion where all of the reagents are added simultaneously, or in a partial step-wise fashion, where fresh or different reagents are added after a given number of steps. For example, if strand separation is induced by heat, and the polymerase is heat-sensitive, then the polymerase will have to be added after every round of strand separation. However, if, for example, a helicase is used for denaturation, or if a thermostable polymerase is used for extension, then all of the reagents may be added initially, or, alternatively, if molar ratios of reagents are of consequence to the reaction, the reagents may be replenished periodically as they are depleted by the synthetic reaction.

Those skilled in the art will know that the PCR process is most usually carried out as an automated process with a thermostable enzyme. In this process, the reaction mixture is cycled through a denaturing region, a primer annealing region, and a reaction region. A machine specifically adapted for use with a thermostable enzyme is disclosed more completely in EP 236,069 (see U.S. Pat. No. 5,038,852, U.S. Ser. Nos. 899,061, filed Aug. 22, 1986, pending, and 833,368, filed Feb. 25, 1986, now abandoned, all of which are incorporated herein by reference) and is commercially available from PECI.

One reason, as noted above, the PCR process is important in the method of the present invention is that the PCR process can be used to amplify the sample nucleic acid prior to HLA DP DNA typing. Another important use of PCR for purposes of the present invention, however is for determining the nucleotide sequence of previously undiscovered allelic variants which exist in the HLA-DP region, so that probes for those variants can be constructed and used in the present method. In this use of the PCR process, polymorphic regions of the DPalpha and DPbeta genes are amplified, and the nucleotide sequences of these polymorphic target regions, for example, the second exon of the DPalpha and DPbeta genes, are determined. As illustrated below, it is also useful for the cells containing a particular variant to be typed by serological typing, mixed lymphocyte typing, or primed lymphocyte typing to correlate the nucleotide sequence of a particular variant with the DP type established by prior art methods.

Analysis of the nucleotide sequence of the target region of a DP variant allele can be readily performed by direct analysis of the PCR products. A preferred sequencing protocol is described by Innis et al., 1988, *Proc. Natl. Acad. Sci.* 85:9436–9440, and in Ser. No. 249,367, filed Sep. 23, 1988, incorporated herein by reference. A process for direct sequence analysis of PCR amplified products is also described by Saiki et al., 1988, *Science* 239:487–491. Alternatively, the amplified target sequence may be cloned prior to sequence analysis, as described by Scharf et al., 1986, *Science* 233:1076–1078.

As discussed in the Examples below, a panel of DPw typed cells, representing a large number of different haplotypes, has been analyzed by PCR and nucleotide sequencing of the second exon of the DPbeta gene. As a result of this effort and similar efforts using samples obtained from a variety of individuals suffering from autoimmune diseases, discussed in greater detail below, 22 different allelic variants in this locus were discovered. In general, the results demonstrated that specific DPbeta sequences correlate with the standard PLT-defined DPw1 through DPw6 specificities. The rare exceptions may reflect the difficulty of obtaining a standard and reproducible PLT DPw typing system, which difficulties highlight the advantages of the present method. In this regard, it is relevant that the cell line Cox, originally typed as DPw1, has recently been retyped as DPw3 and contains the DPB3 allele.

Other interesting and important correlations between the serologically defined DP types and DP variant nucleotide sequences have been discovered as a result of the advances provided by the present invention. For instance, the DPw4 type of the prior an can now be subdivided into two DPbeta subtypes (designated DPB4.1 and DPB4.2) by the method of the present invention. The DPB4.2 allele was found in two (APD and LBI) DPw4 homozygous typing cells (HTCs) known to have an unusual DPw4 typing. DPbeta subtypes (designated DPB2.1 and DPB2.2) for the DPw2 type were also discovered as a result of the present invention.

Yet another significant advance provided-by the present invention relates to the discovery of a large number of variant DPbeta alleles in a variety of cells that type by the prior art methods as DP "blank." These variant alleles have been designated with DPB numbers of 7 and above. Further analysis of DPw blank haplotypes will probably lead to the identification and characterization of additional DPbeta alleles that can then be typed by the present method. DPw blank cells are those which fail to stimulate the existing PLT panels of T cell reagents. Unlike the serologic DQw blank specificity, which, as described by Horn et al., 1988, *Proc. Natl. Acad. Sci. U.S.A.* 85:6012–6016, is encoded by a unique DQB sequence, the DPw blank specificity is heterogeneous. Because the haplotypic frequency of the DPw blank is estimated to be 40%, the present invention is especially important in that it for the first time enables the subtyping of this large DPw type.

The availability of DPbeta DNA sequences from DPw typed cells not only makes possible the subdivision of the serological DPw types but also makes possible the identification of the linear epitopes defined by serologic and cellular typing reagents. For example, the antibody SP42 reacts with DPw2 and DPw4 cells. The only sequence unique to these two specificities is the GlyGlyProMet (GGPM) at positions 84 to 87, which are therefore believed to constitute the SP42 epitope. Likewise, the antibody SP3 reacts with DPw3 and DPw6 cells, as well as with some additional cells like the DPw blank lines Tok and Akiba. These lines bear the specificity Cp63 and contain the closely related DPbeta alleles DPB9 and DPB12. The only sequence unique to SP3 reactive cells is the acidic AspGluAsp (DED) sequence at positions 55 to 57. The SP3 epitope therefore seems to map to this region of the DPbeta chain.

As yet another example of how the novel DP sequences of the invention allow the mapping of serologically defined epitopes, the antibody DP11.1 reacts with DPw2 and DPw4 cells. Bodmer et al., 1987, *Proc. Acad. Sci. U.S.A.* 84:1644–1648, showed with Western blot analysis that this antibody binds to the DPalpha chain. Given the pattern of DPbeta polymorphisms provided by the present invention, this observation suggests that the DP11.1 antibody binds to a conformational determinant formed by the DPalpha chain and DPbeta chains containing the GlyGlyProMet (GGPM) sequence at positions 84 to 87.

Polymorphic residues in the HLA DP region may also constitute epitopes recognized by T cell clones. Cells from clone 1666 react with DPw5 and some DPw2 cells. ABL (DPB2.2) is positive and WPV (DPB2.1) is negative, as disclosed at the Tenth International Histocompatibility Workshop. These C1666 cells may recognize the GluAlaGlu (EAE) residues at position 55 to 57, because this sequence is unique to the DPB2.2 and DPB5 alleles. A Leu (as opposed to Phe) residue at position 35 is also unique to C1666 reactive cells.

The same approach of correlating specific polymorphic residues with DPw specificities can be used to map the epitopes defined by PLT typing. For example, the only difference between the DPB2.1 and DPB4.2 alleles is the Glu to Lys change at position 69. Because cells containing these alleles are distinguished from each other in the PLT system, the charge of the polymorphic position 69 residue is believed to be involved in the epitope recognized by PLT typing cells. Similarly, the only differences between the DPB3 and DPB6 alleles is the Lys to Glu substitution at position 69, as well as Val to Met change at position 76.

As illustrated by the foregoing, the novel DPbeta sequences provided by the present invention not only provide the basis for a very useful DPbeta DNA typing method but provide much useful information in the interpretation of serological DPbeta typing results. The present invention also enables one to perform HLA DNA typing not only on the DPbeta locus but also on the DPalpha locus as well. As illustrated below, at the present time, only two variant alleles are known to exist at the second exon of the DPalpha locus (see Trowsdale et al., supra). The protein sequences encoded by the second exon of these two alleles (these alleles are designated DPA1 and DPA2) differ from each other by only three amino acids, and these differences do not appear to correlate with any specific PLT-defined type. Thus, the DPalpha variation is much less extensive than predicted by the RFLP variation detected with DPalpha probes (see Hyldig-Nielsen et al., 1987, *Proc. Natl. Acad. Sci. U.S.A.* 84:1644–1648), suggesting that most of the polymorphisms detected in the DPalpha gene by RFLP analysis are either in noncoding sequences or in a nearby DPbeta locus. The observed correlations between DPw types and DPalpha RFLP markers therefore probably reflects linkage disequilibrium between DPbeta sequence variation and the polymorphic restriction sites detected with the DPalpha probe, as does the association between DRalpha RFLP markers and DR specificities (see Stetler et al., 1985, *Proc. Natl. Acad. Sci. U.S.A.* 82:8100–8104).

The DNA sequences of the DPalpha and DPbeta genes serve as a useful starting point in the design of the sequence specific oligonucleotide probes of the present invention. These probes are designed so that, under stringent hybridization conditions, the probes hybridize specifically only to exactly complementary sequences in variant segments of the DPalpha and DPbeta alleles. These SSO probes may be of any length which spans the variant sequences in a variant region and allows for sequence specific hybridization, but preferably the hybridizing region of the probe is short, in the range of 10 to 30 bases, and more preferably is about 17 to 19 bases in length. For immobilization, the probe may also contain long stretches of poly T which can be fixed to a solid support by irradiation, a technique described in more detail in PCT Patent Publication No. WO 89/11548 and Ser. No. 347,495, filed May 4, 1989, now abandoned, which is a continuation-in-part of Ser. No. 197,000, filed May 20, 1988, now abandoned, all of which are incorporated herein by reference.

The SSO probes of the invention are also designed to hybridize specifically with a particular variant segment of a DP allele and to have destabilizing mismatches with the other variant sequences known for the particular segment. Preferably, the probes are specific for variant DNA segments in the variable second exons of the DPalpha and DPbeta genes, and even more preferably, the probes are specific for DNA segments encoding the residues near positions 8–11, 36, 55–57, 65–69, 76, and 84–87 of the second exon. Oligonucleotide probes which have been designed to hybridize specifically to the second exons of the DP-beta and DP-alpha alleles are described in more detail below and in the Examples.

The probes of the invention can be synthesized and labeled using the techniques described above in the discussion of PCR primers. For example, the probe may be labeled at the 5'-end with $^{32}$P by incubating the probe with $^{32}$P-ATP and kinase. A suitable non-radioactive label for SSO probes is horseradish peroxidase (HRP). Methods for preparing and detecting probes containing this label are described in the Examples below and in now abandoned Ser. No. 178,276, filed Apr. 6, 1988, and incorporated herein by reference. For additional information on the use of such labeled probes, see U.S. Pat. No. 4,789,630; Saiki et al., 1988, *N. Eng. J. Med.* 319:537–541; and Bugawan et al., 1988, *Bio/Technology* 6:943–947, incorporated herein by reference. Useful chromogens include red leuco dye (see Ser. No. 136,166, filed Dec. 18, 1987) and TMB.

The probes of the invention can be used to identify the allelic sequences present in a sample by determining which of the SSO probes bind to the HLA DP sequences present in the sample. Suitable assay methods for purposes of the present invention to detect hybrids formed between SSO probes and nucleic acid sequences in a sample are known in the art. For example, the detection can be accomplished using a dot blot format, as described in the Examples. In the dot blot format, the unlabeled amplified sample is bound to a membrane, the membrane incubated with labeled probe under suitable hybridization conditions, unhybridized probe removed by washing, and the filter monitored for the presence of bound probe. When multiple samples are analyzed with few probes, a preferred process requires high stringency hybridization and wash conditions, allowing only perfectly matched hybrids to exist.

An alternative method is a "reverse" dot blot format, in which the amplified sequence contains a label. In this format, the unlabeled SSO probes are bound to the membrane and exposed to the labeled sample under appropriately stringent hybridization conditions. Unhybridized labeled sample is then removed by washing under suitably stringent conditions, and the filter is then monitored for the presence of bound sequences. In another version of the "reverse" dot blot format, the SSO probe is labeled, and the sample nucleic acid is unlabeled. After hybridization and washing, the labeled probe, or a labeled fragment of the probe, is released from the membrane and detected to determine if a sequence in the sample hybridized to the labeled oligonucleotide. Release of label can be achieved by digestion with a restriction enzyme that recognizes a restriction site in the duplex hybrid. This procedure, known as oligomer restriction, is described more fully in U.S. Pat. No. 4,683,194 and corresponding EP Patrny Publication 164,054, incorporated herein by reference.

Whatever the method for determining which DP SSO probes of the invention hybridize to DP sequences in a sample, the central feature of the DP DNA typing method involves the identification of the HLA DP alleles present in the sample by analyzing the pattern of binding of a panel of SSO probes. Although single probes of the invention can certainly be used to provide useful information, the variation in the DPbeta alleles is dispersed in nature, so rarely is any one probe able to identify uniquely a specific DP variant. Rather, as shown in the Examples, the identity of an allele is inferred from the pattern of binding of a panel of SSO probes, which are specific to different segments of the DPalpha and DPbeta genes.

DNA typing of HLA DP alleles is useful for many different purposes. For example, DPbeta polymorphism is involved in tissue rejection of allografts. Bone marrow transplantation studies revealed that three apparently HLA-identical donor-recipient pairs who exhibited acute graft versus host disease and weak MLC reactivity were, by RFLP analysis, all different in the DP region, as described by Amar et al., *J. Immunology* 138:1947. Thus, useful methods for preventing graft rejection will involve matching the HLA DP types of the donor and recipient by applying the present method of HLA DP DNA typing: inferring the HLA alleles present in donor and host from the pattern of hybridization of SSO probes to DPbeta and/or DPalpha nucleic acid sequences present in samples obtained from both donor and host.

Another important application for the present method of HLA DP DNA typing is in determining an individual's susceptibility to autoimmune diseases linked to certain HLA DP alleles. The association of particular DP alleles with an autoimmune disease can be discovered by using the present method to determine the frequency with which a given allele is present in individuals suffering from the autoimmune disease and comparing that frequency with the frequency determined for healthy individuals of a control group, as has been done with other HLA typing systems. For example, Howell et al., 1988, *Proc. Natl. Acad. Sci. U.S.A.* 85:222–226, reported a significant association between coeliac disease (CD) and a pair of HLA DPalpha and HLA DPbeta RFLPs. Such studies often provide the additional benefit of the discovery of previously uncharacterized DP alleles, in both patient and control groups. For instance, the DPB13 through DPB19 alleles, the sequences of which represent an important aspect of the present invention, were discovered in the course of studies involving autoimmune disease patients and control groups.

In just such a fashion, an initial study of four CD patients who were typed by the method of the present invention revealed that the DPB4.2 allele confers CD susceptibility, A more extensive study, based on samples from Italian individuals, also showed that the calculated relative risk (RR) of CD for the DPB4.2 allele is 9.3 and that six of the eleven CD patients typed by the present method carried the DPB3 allele. About 78% of CD patients examined by the present method carry either the DPB4.2 or the DPB3 alleles, so that the RR for the presence of either of these alleles is 13.5. In yet another study of U.S. individuals with CD, an increase in the DPB1 allele frequency, as well as an increase in the DPB9 and DPB4.2 allele frequency, was observed when compared to the frequency of these alleles in a control group. Such studies also revealed that specific combinations of DQbeta alleles (DQB2), DQalpha alleles (DQA4) and DPbeta alleles (DPB4.2 or DPB3) are associated with increased risk of CD susceptibility.

As shown from the foregoing, the present invention provides important new methods for determining the CD susceptibility of an individual, which methods comprise determining whether an individual carries a DP allele associated with CD susceptibility. As shown herein, such CD susceptibility-conferring alleles include the DPB9, DPB4.2, DPB3, and DPB1 alleles, and as DPB4.1 is a relatively common allele, there is an increased frequency of the genotype DPB4.1/4.2 in CD susceptible individuals.

As with CD, the present invention provides similar advances with respect to other serious autoimmune diseases. For instance, studies that correlate allelic frequency with disease show that the frequency of specific DPbeta alleles appears to be higher in insulin dependent diabetes mellitus (DDM) and myasthenia gravis (MG) patients than in otherwise HLA matched controls. For MG, the frequency of DP alleles that code for the sequence DEAV at the 3' end of the second exon, such as DPB3 and DPB5, is increased. In addition, the frequency of the DPB4.1 allele in MG patients (relative to healthy control individuals) is dramatically decreased, suggesting that DPB4.1 may confer protection from MG. For IDDM, the frequency of DPbeta alleles DPB2.1, DPB1, DPB4.1, and DPB13 is increased. Many of the DDM patients studied that carried the DPB13 allele also carried the HLA alleles B 18 and DR3.

The DP typing methods of the present invention have also provided important advances in determining whether an individual is susceptible to certain forms of arthritis. For instance, patients with classical rheumatoid factor positive adult rheumatoid arthritis (ARA) show an increased frequency of the DPB4.2 allele, although more studies must be completed to ensure that this increase is statistically significant. In addition, scientists have long known that the DPw2 serologic type is associated with susceptibility to pauciarticular juvenile rheumatoid arthritis (JRA). As noted above, the present invention has for the first time allowed the serologic DPw2 type to be subdivided into two DPB DNA types, and the disease-susceptibility typing methods of the present invention demonstrate that the known DPw2-associated susceptibility to JRA is more specifically attributable to the DPB2.1 allele. About 55% of the JRA patients examined were positive for DPB2.1, while only 16% of control individuals had this allele, giving a RR of 6.3 for JRA in individuals with the DPB2.1 allele. The association of JRA with the DPB2.1 allele is independent of linkage with previously defined HLA DP region markers, and the significance of this DPB2.1 association with JRA can be more readily appreciated when one considers that the DPB2.1 sequence differs from the DPB4.2 allele (apparently not associated with JRA susceptibility) by only one amino acid at position 69 of the B 1 domain. It should be noted, however, that most JRA patients with the DPB2.1 allele also had a disease-associated DR marker such as DRw8, DR5, or DRw6.

Thus, the present invention also provides a method for detecting JRA susceptibility that comprises treating HLA DP genomic DNA of an individual, preferably after amplification, with oligonucleotide probes specific for the DPB2.1 allele and determining if hybridization has occurred. General practice of the invention will, however, utilize the full panel of DPbeta probes. As noted above, the present method will be useful in determining the DP association with a wide variety of autoimmune diseases, not just JRA. This fact can be more readily grasped by considering the Table below, in which the allelic frequency (number of alleles of the indicated DP type divided by total number of DP alleles present and then multiplied by 100) for the various DP alleles in a number of patient groups and a control group is shown. In the Table, MS indicates multiple sclerosis patients.

| | HLA-DP ALLELIC FREQUENCIES IN SELECTED PATIENT GROUPS | | | | |
|---|---|---|---|---|---|
| Allele | Controls (n = 50) | MG (n = 23) | JRA (n = 44) | MS (n = 21) | ARA (n = 23) |
| 1 | 6% | 9% | 3% | 2% | 5% |
| 2.1 | 10% | 6% | 30% | 12% | 12% |
| 2.2 | 0% | 2% | 0% | 6% | 0% |
| 3 | 6% | 13% | 11% | 17% | 11% |
| 4.1 | 56% | 25% | 40% | 48% | 41% |
| 4.2 | 10% | 10% | 6% | 6% | 22% |
| 5 | 2% | 10% | 0% | 0% | 2% |
| 6 | 2% | 0% | 2% | 0% | 2% |
| 7 | 0% | 0% | 0% | 2% | 0% |
| 8 | 0% | 6% | 0% | 0% | 0% |
| 9 | 0% | 6% | 1% | 0% | 0% |
| 10 | 1% | 6% | 1% | 0% | 2% |
| 11 | 3% | 2% | 1% | 0% | 0% |
| 12 | 0% | 0% | 0% | 0% | 0% |
| 13 | 1% | 2% | 1% | 2% | 0% |
| 14 | 2% | 0% | 0% | 2% | 2% |
| 15 | 0% | 0% | 2% | 0% | 2% |
| 16 | 0% | 0% | 1% | 2% | 0% |
| 17 | 1% | 2% | 0% | 0% | 2% |
| 18 | 0% | 0% | 0% | 0% | 0% |
| 19 | 0% | 0% | 0% | 0% | 0% |
| 20 | 0% | 2% | 0% | 0% | 0% | n = number of individuals typed; 2n is the number of chromosomes tested; controls were individuals from Northern California.

In general, these studies of autoimmune disease suggest that the charge of polymorphic residues at positions 55, 56, and 69 of the DPbeta chain are involved in genetic susceptibility to autoimmune disease. For instance, the change at position 55 from alanine to aspartate occurs in both the DPB2.1 and DPB4.2 alleles; however, in IDDM, which appears to be linked to DPB2.1, there is also a change in the amino acid at position 69. It should be noted, though, that is is the entire allele, and not simply an amino acid at one position in an allele, which appears to confer susceptibility.

The effect of the HLA DP alleles on autoimmune disease susceptibility reflects similar findings in the HLA DR and HLA DQ loci. For instance, Scharf et al., 1988, *Proc. Natl. Acad. Sci. U.S.A.* 85:3504–3508, and Horn et al., 1988, *Proc. Natl. Acad. Sci. U.S.A.* 85:6012–6016, report that polymorphic residues at position 57 of the DQbeta chain and position 70 of the DRbeta I chain are implicated in genetic susceptibility to the autoimmune diseases pemphigus vulgaris (PV) and IDDM.

As noted above, it is anticipated that as medical technology develops, more disease or disease-prone states, including Grave's disease, S. L. E., and Sjögren's Syndrome, will become known to be associated with various DP alleles. The present invention provides methods for distinguishing such alleles from other alleles and so provides a means to identify individuals at high risk for an autoimmune disease. In a preferred embodiment, an individual whose susceptibility is to lye determined is analyzed for HLA DP type first by using the PCR method to amplify the target region of the HLA DP locus. Then, SSO probes are hybridized to the amplified target region, and the particular DP allele present in the amplified DNA is determined from the pattern of binding of the SSO probes. Finally, one determines whether the allele present in the amplified DNA is an allele associated with the autoimmune disease.

The present method, however, is not limited to the field of medical science in ability to provide significant benefits. DNA typing methods also now play a significant role in the important area of individual identification, whether for solving crimes, as when the identity of a criminal or victim is established by linking an individual with evidence left at the scene of a crime, or for solving other issues of a non-criminal nature, as when biological material is used to determine the maternity or paternity of an individual.

Whatever the purpose for which the present invention is employed, the differences between various DP alleles is key to the success of the method. The most significant differences between DP alleles can be detected quite readily when the various amino acid sequences encoded by the alleles are aligned and examined. Such an alignment is shown below, where a dash indicates identity with the DPB4.1 allele (for the various DPbeta alleles and the DPbeta pseudogene, designated SXB) or with the DPA1 allele (for the DPalpha DPA2 allele and the DPalpha pseudogene, designated SXA). In this depiction, the numbered positions are for the mature peptide subunits, allele designations are at left, and representative cell sources are at right.

DPalpha Alleles

```
                10          20          30          40          50          60          70          80
DPA1:  DHVSTYAAFVQTHRPTGEFMFEFDEDEMFYVDLDKKETVWHLEEFGQAFSFEAQGGLANIAILNNNLNTLIQRSNHTQATN   (LB)
DPA2:  ----------------------------Q-------------------R-----------------------A-       (Daudi)
(SXA): ----E-------S--Y--------E-Q---N--E--M--P--IHT-D-G--R-I-G-VMARKH---R-NG KQ-W--D
```

DPbeta Alleles

```
                10          20          30          40          50          60          70          80          90
DPB4.1: NYLFQGRQECYAFNGTQRFLERYIYNREEFARFDSDVGEFRAVTELGRPAAEYWNSQKDILEEKRAVPDRMCRHNYELGGPMTLQRR  (HHK)
DPB4.2: ------------------------------------------------DE---------------------------------     (APD)
DPB2.1: -------------------------V-----------------------DE-----------E------------------        (LB)
DPB2.2: -------------------------V------------------------E-----------E------------------        (QBL)
DPB8:   ----------------LV-------V------------------------DE-----------E----V--DEAV-----        (Plaz)
DPB5:   -------------------------V------------------------E------------------DEAV-----         (HAS)
DPB7:   ----------------LV-------V------------------------E-----------E------V--DEAV-----       (Raji)
DPB3:   VY-L---------------------V-----------------------DED-----L-----E------V--DEAV-----      (SLE)
DPB6:   VY-L---------------------V-----------------------DED-----L-----E------V--DEAV-----      (JMOS)
DPB11:  VY-L-------------------Q-Y-----------------------DE------L---R-E------V--DEAV-----      (CRK)
DPB13:  VY-L---------------------Y-----------------------DE-------------E------I--DEAV-----     (BH)
DPB1:   VY-----------------------Y-----------------------DE-------------E------V--DEAV-----     (LUY)
DPB10:  VH-L---------------------V-----------------------DE-------------E------V--DEAV-----     (BM21)
DPB9:   VH-L---------------------V-----------------------DED-----------E------V--DEAV-----      (TOK)
DPB12:  -VH-L----G-------------S-V-----------------------DED-----------E------V--R--DEAV---     (AKIBA)
DPB14:  VH-L---------------------V-----------------------DED-----L-----E------V--DEAV-----      (8268)
DPB15:  VY---------------------Q-Y-----------------------DE------L-----E------V---V------       (PLH)
DPB16:  ----L--------------------V-----------------------DE-------------E------V--DEAV---       (JRA)
DPB17:  VH-L---------------------V-----------------------DE-------------E------V--DEAV-----     (JRAB)
DPB18:  VY-----------------------V-----------------------DE-------------E------V----------      (JCA)
DPB19:  ----L--------------------V-----------------------E-------------DE------I--DEAV-----     (CB68)
DPB20:  VH-L---------------------V-----------------------DED-----L-----E------V--DEAV-----
SXB:    -SVY-E---------VVDGL----YVH---A-----L--M-----IG--F------FM-R--EV-KV---K--ME-LIR---     (Priess)
```

To detect and distinguish between DP alleles in a practicable and economic fashion, however, one must know the nucleotide sequence of the alleles. Portions of the nucleotide sequences of various DPalpha and DPbeta alleles are shown below; the sequences are identified as above. The illustrative primers of the invention enable production of DNA from which the sequence of codons 8 to 90 can be determined. The location of allele sequences that are the preferred target sequences for hybridization with the various probes of the invention are designated as l-A-l, l-B-l, l-C-l, l-D-l, l-E-l, and l-F-l.

```
                      +10              +15              +20              +25
           Asn Tyr Leu Phe Gln Gly Arg Gln Glu Cys Tyr Ala Phe Asn Gly Thr Gln Arg Phe Leu Glu Arg Tyr
DPB4.1:    AGAATTACCTTTTCCAGGGACGGCAGGAATGCTACGCGTTTAATGGGACACAGCGCTTCCTGGAGAGATAC

DPB4.2:    ------------------------------------------------------------------------

DPB2.1:    ------------------------------------------------------------------------

DPB2.2:    ------------------------------------------------------------------------

DPB8:      ------------------------------------------------------------------------

DPB5:      ------------------------------------------------------------------------

DPB7:      ------------------------------------------------------------------------

DPB3:           G-G-A----TT-------------------------------------------------------

DPB6:           G-G-A----TT-------------------------------------------------------

DPB11:          G-G-A----TT-------------------------------------------------------

DPB12:     --------G-G-A----TT---------------GC----------------------A-----T---

DPB13:          G-G-A----TT-------------------------------------------------------

DPB1:           G-G-A---------------------------------------------------------------

DPB9:           G-GCA----TT-------------------------------------------------------

DPB10:          G-GCA----TT-------------------------------------------------------

DPB14:          G-GCA----TT-------------------------------------------------------

DPB15:          G-G-A---------------------------------------------------------------

DPB16:          ------------------------------------------------------------------

DPB17:          G-GCA----TT-------------------------------------------------------

DPB18:          G-G-A---------------------------------------------------------------

DPB19:          ------------------------------------------------------------------

DPB20:          G-GCA----TT-------------------------------------------------------
                l------A-----l

+30              +35              +40              +45              +50
           Ile Tyr Asn Arg Glu Glu Phe Ala Arg Phe Asp Ser Asp Val Gly Glu Phe Arg Ala Val Thr Glu Leu
DPB4.1:    ATCTACAACCGGGAGGAGTTCGCGCGCTTCGACAGCGACGTGGGGGAGTTCCGGGCGGTGACGGAGCTG

DPB4.2:    ------------------------T---------------------------------------------

DPB2.1:    ------------------------T---------------------------------------------

DPB2.2:    --------------------C---T---------------------------------------------

DPB8:      ------------------------T---------------------------------------------

DPB5:      --------------------C---T---------------------------------------------

DPB7:      ------------------------------------------------------------------------

DPB3:      ------------------------T---------------------------------------------

DPB6:      ------------------------T---------------------------------------------

DPB11:     ------------C------A------------------------A-------------------------

DPB12:     ------------------------T---------------------------------------------

DPB13:     --------------------A---------------A-----------------------------------

DPB1:      --------------------A---------------------------------------------------

DPB9:      ------------------------T---------------------------------------------
```

-continued

```
DPB10:  ---------------------T----------------------------------------
DPB14:  ---------------------T----------------------------------------
DPB15:  -----------C------A-----------------------A-------------------
DPB16:  ---------------------T----------------------------------------
DPB17:  ---------------------T----------------------------------------
DPB18:  ---------------------T----------------------------------------
DPB19:  ---------------------T----------------------------------------
DPB20:  ---------------------T----------------------------------------
                  |------B------|
```

```
           +55              +60              +65              +70
        Gly Arg Pro Ala Ala Glu Tyr Trp Asn Ser Gln Lys Asp Ile Leu Glu Glu Lys Arg Ala Val Pro
DPB4.1: GGGCGGCCTGCTGCGGAGTACTGGAACAGCCAGAAGGACATCCTGGAGGAGAAGCGGGCAGTGCCG
DPB4.2: ----------A--A--------------------------------------------------
DPB2.1: ----------A--A-----------------------------------G--------------
DPB2.2: ----------AG-------------------------------------G--------------
DPB8:   ----------A--A-----------------------------------G--------------
DPB5:   ----------AG-------------------------------------G--------------
DPB7:   ----------------------------------------------------------------
DPB3:   ----------A--A---C----------------------C-----------------------
DPB6:   ----------A--A---C----------------------C--------G--------------
DPB11:  --------------------------------------------------G--------------
DPB12:  ----------A--A---C--------------------------------G--------------
DPB13:  -------------------------------------------------G--------------
DPB1:   ----------------------------------------------------------------
DPB9:   ----------A--A---C--------------------------------G--------------
DPB10:  ----------A--A-----------------------------------G--------------
DPB14:  ----------A--A---C----------------------C-----------------------
DPB15:  ----------------------------------------C--------G--------------
DPB16:  ----------A--A-----------------------------------G--------------
DPB17:  ----------A--A---C--------------------------------G--------------
DPB18:  ----------A--A---------------------------------------------------
DPB19:  ----------AG-------------------------------------G--------------
DPB20:  ----------A--A---C----------------------C-----------------------
                  |---C----|                    |------D-------|
```

```
           +75              +80              +85              +90
        Asp Arg Met Cys Arg His Asn Tyr Glu Leu Gly Gly Pro Met Thr Leu Gln Arg Arg
DPB4.1: GACAGGATGTGCAGACACAACTACGAGCTGGGCGGGCCCATGACCCTGCAGCGCCGAG
DPB4.2: ----------------------------------------------------------
DPB2.1: ----------------------------------------------------------
PB2.2:  ----------------------------------------------------------
DPB8:   ------G-A-------------------A--A-G--G---------------------
DPB5:   ----------------------------A--A-G--G---------------------
DPB7:   ------G-A-------------------A--A-G--G---------------------
DPB3:   ------G-A-------------------A--A-G--G---------------------
```

```
-continued
DPB6:   ------------------------A--A-G--G----------
DPB11:  ------------------------A--A-G--G----------
DPB12:  ------G-A-------G-------A--A-G--G----------
DPB13:  --------A---------------A--A-G--G----------
DPB1:   ------G-A---------------A--A-G--G----------
DPB9:   ------G-A---------------A--A-G--G----------
DPB10:  ------G-A---------------A--A-G--G----------
DPB14:  ------G-A---------------A--A-G--G----------
DPB15:  ---------------------------T---------------
DPB16:  ------------------------A--A-G--G----------
DPB17:  ------------------------A--A-G--G----------
DPB18:  ---------------------------T---------------
DPB19:  --------A---------------A--A-G--G----------
DPB20:  ------------------------A--A-G--G----------
        |-E-|                    |----F----|
```

The DNA sequences provided above are an important aspect of the present invention. Although only one strand of the sequence is shown, those of skill in the art recognize that the other strand of the sequence can be inferred from the information depicted above. This information enables the construction of the probes of the invention. Many illustrative probes of the invention are shown in the Examples below. However, suitable SSO probes for hybridization analysis of the DPbeta alleles will comprise (or be complementary to) certain polymorphic sequences. Six sets of illustrative probes of the invention are depicted below; each set is designed to distinguish between the polymorphisms in a specific segment of the second exon of the HLA DPbeta gene. The designation of the segments is as described above. The polymorphic residues encoded within the allelic variant in the segment to which a probe hybridizes is shown in one letter amino acid code (the dash means that prototypic residues are present in those positions) to the left of the probe sequence. The probes span the regions encoding the polymorphic amino acid residues and are shown as having a length of about 18 nucleotides. Those sequences in the probe that encode the polymorphic amino acid residues, and thus must be included within a probe for detecting the alleles that encode the designated segment, are between the slash marks in the sequence. The DP alleles with which the probe will hybridize are shown to the right of the probe.

HLA DPbeta SSO Probes

| | Amino Acid | Probe Sequence | DPbeta Alleles |
|---|---|---|---|
| Segment A: | LF-G: | TAC\CTTTTCCAGGG\ACGG | 2.1, 2.2, 4.1, 4.2, 5, 7, 8, 19 |
| | VY-L: | TAC\GTGTACCAGTT\ACGG | 3, 6, 11, 13 |
| | VY-G: | TAC\GTGTACCAGGG\ACGG | 1, 15, 18 |
| | VH-L: | TAC\GTGCACCAGTT\ACGG | 9, 10, 12, 14, 17, 20 |
| Segment B: | E-FA: | CGG\GAGGAGTTCGC\GCGC | 4.1, 7 |
| | E-FV: | CGG\GAGGAGTTCGT\GCGC | 2.1, 3, 4.2, 6, 8, 9, 10, 12, 14, 16, 17, 18, 19, 20 |
| | E-LV: | CGG\GAGGAGCTCGT\GCGC | 2.2, 5 |
| | Q-YA: | CGG\CAGGAGTACGC\GCGC | 11, 15 |
| | E-YA: | CGG\GAGGAGTACGC\GCGC | 1, 13 |
| | E-FV: | CGG\GAGGAATTCGT\GCGC | 10 |
| Segment C: | AAE: | CCTG\CTGCGGAG\TACTGG | 1, 4.1, 7, 11, 13, 15 |
| | DEE: | CCTG\ATGAGGAG\TACTGG | 2.1, 4.2, 8, 10, 16 |
| | EAE: | CCTG\AGGCGGAG\TACTGG | 2.2, 5, 19 |
| | DED: | CCTG\ATGAGGAC\TACTGG | 3, 6, 9, 12, 14, 17, 20 |
| Segment D: | I---K: | GAC\ATCCTGGAGGAGAA\G | 1, 4.1, 4.2, 5, 7, 18 |
| | I---E: | GAC\ATCCTGGAGGAGGA\G | 2.1, 2.2, 8, 9, 10, 12, 13, 16, 17 |
| | L---K: | GAC\CTCCTGGAGGAGAA\G | 3, 14, 20 |
| | L---E: | GAC\CTCCTGGAGGAGGA\G | 6 |
| | L---R: | GAC\CTCCTGGAGGAGAG\G | 11, 15 |
| Segment E: | M: | GACAGG\ATG\TGCAGACAC | 2.1, 2.2, 4.1, 4.2, 5, 6, 11, 15, 16, 17, 18, 20 |
| | V: | GACAGG\GTA\TGCAGACAC | 1, 3, 7, 8, 9, 10, 12, 14 |
| Segment F: | GGPM: | CTGG\GCGGGCCCA\TGACC | 2.1, 2.2, 4.1, 4.2 |

| | HLA DPbeta SSO Probes | |
|---|---|---|
| Amino Acid | Probe Sequence | DPbeta Alleles |
| DEAV: | CTGG\ACGAGGCCG\TGACC | 1, 3, 5, 6, 7, 8, 9, 10, 11 |
| VGPM: | CTGG\TCGGGCCCA\TGACC | 15, 18 |

Because the probes of the invention are single stranded for use in hybridization, it is important to note that merely because a probe is designed to hybridize with, for example, the coding strand, does not mean that an equally useful probe could not be designed that would hybridize to the complementary sequence present on the noncoding strand.

The sequence information provided above also relates to other important aspects of the invention. The preferred primers of the invention are designed to amplify many different DP alleles. In many instances, as demonstrated in the Examples below, such primers are very useful. However, those of skill in the art recognize that the DNA sequence information provided above can also be used to design primers that will enable allele specific amplification. Such allele-specific primers will only amplify a single allele or a certain subset of known alleles. For example, the "DEAV" probes of the invention can be used as one primer of a primer pair to provide for allele-specific amplification of "DEAV" DPbeta alleles.

The present invention also relates to kits that comprise a multicontainer unit comprising essential components for practicing the present method. For example, the kit can contain primers for PCR, as such primers are necessary in the preferred embodiment of the invention. These primers will amplify at least the DPbeta gene, and, when appropriate, for example in forensic analysis, primers can be included that also amplify the DPalpha gene. The kit must also contain SSO probes for at least the DPbeta gene, and, when appropriate, for the DPalpha gene as well. In some cases, the SSO probes may be fixed to an appropriate support membrane which is useful for the hybridization analysis. Other optional components that may be contained in containers within the kit include, for example, an agent to catalyze the synthesis of primer extension products, the substrate nucleosides triphosphates, means used to label (for example, an avidin-enzyme conjugate and enzyme substrate and chromogen if the label is biotin), and the appropriate buffers for PCR or hybridization reactions. In addition to the above components, the kit can also contain instructions for carrying out the present method.

A number of examples of the present invention, which are provided only for illustrative purposes and not to limit the scope of the invention, are presented below. Numerous embodiments of the invention within the scope of the claims that follow the examples will be apparent to those of ordinary skill in the art from reading the foregoing text and following examples. In the following examples, certain techniques were standard, unless specifically indicated otherwise. Such techniques include PLT, which was performed essentially as described by Shaw et al., 1980, *J. Exp. Med.* 152:565–580. Generally, for lymphocyte priming, responder and stimulator cells were thawed, washed, and resuspended in RPMI-1640 medium supplemented with glutamine and antibiotics (complete media). Responding cells were mixed with irradiated stimulator cells in a ratio of 2:1, and the cell mixture was incubated for ten days at 37 degrees C. The primed irradiated stimulator cells were co-cultured with irradiated stimulator cells in complete media. After 48 hours, $^3$H-thymidine was added to the culture. The cells were harvested 18 hours later, and tritium incorporation was evaluated by counting beta-emission.

DNA sequence analysis was performed as described by Maniatis et al., *Molecular Cloning: A Laboratory Manual* (New York, Cold Spring Harbor Laboratory, 1982). Generally, the sequences to be analyzed were cloned into an M13 cloning vector and analyzed by either the Maxam-Gilbert technique or by the dideoxy chain termination technique. Synthetic oligonucleotides, both primers and probes, were synthesized using commercially available instruments and techniques well known in the art.

EXAMPLE 1

Analysis of the DNA Sequences of HLA DP Alleles

The DNA sequences of the variable second exons of a variety of alleles of the DPalpha gene and of the DPbeta gene were determined. The DNA samples used were chosen to represent as wide a spectrum of PLT defined DP alleles as possible. DNA was extracted from cell lines homozygous for the standard six DPw types, from cells exhibiting unusual typing reactions, and from cells exhibiting DP blank reactions. DNA extraction was by standard techniques, as described by Maniatis et al., in *Molecular Cloning: A Laboratory Manual*. The variable second exons of the DPalpha and the DPbeta genes were amplified by the PCR method, as described. The amplified DNA sequences were cloned into an M13 derived vector, and the DNA sequences were determined by the chain termination method. The cell lines used, their DR serotypes, their PLT defined DPw types, and the DNA defined alleles they were found to contain are listed in tabular form below (blank spaces indicate data not determined).

| Cell Line | DR Type | DPw Type | DPB Alleles | DPA Alleles |
|---|---|---|---|---|
| CRK | 7 | 1* | 1, 11 | |
| RSO101 | w6 | 1, 3 | 1, 3 | |
| BMG | 4 | 1, 4 | 4.1 | |
| QBL | 3 | 2 | 2.2 | 1 |
| WJR | 2 | 2 | 2.1 | |
| PJM | 3 | 2, 3 | 2.1, 3 | |
| RMD | 5, w13 | 2, 4 | 2.1, 4.1 | |
| JMOS | 4, 5 | 2, 6 | 2.1, 6 | |
| SLE | w13 | 3 | 3 | 1 |
| COX | 3 | 3 | 3 | 1 |
| OPR | w8, w10 | 3, 4 | 3, 4.1 | |
| JAH | 4 | 3, 4 | 3, 4.1 | |
| MRI | 1, 2 | 3, 5 | 3, 5 | |
| HHK | w6 | 4 | 4.1 | |
| LB1 | 3, 7 | 4, MAS | 1, 4, 4.2 | |
| APD | w6 | 4* | 2, 4 | |
| LUY | w8 | 1, 4 | 1, 4.1 | 1, 2 |
| WDV | w6 | 2, 4 | 2.1, 4.1 | |
| SMF | 2, w12 | 4, 5 | 4.1, 5 | |
| BCR | 4, w6 | 4, 6 | 4.1, 6 | |
| GTER | w8, 9 | 5 | 5 | |
| HAS | 4 | 5 | 5, 19 | |

| Cell Line | DR Type | DPw Type | DPB Alleles | DPA Alleles |
|---|---|---|---|---|
| DKY | 9 | 5 | 2.1 | 1 |
| BIN40 | 4 | 3, 6 | 3, 6 | 1 |
| LG2 | 1 | ? | 4.1 | |
| PIAZ | 2.7 | | 8 | |
| TOK | 2 | | 9 | 2 |
| BM21 | w11 | | 10 | |
| VLA | 2, 3 | | 11 | |
| GBA | 1, 7 | | 11 | |
| CD1 | 3, 4 | 3, 6 | 10 | |
| CD2 | 7, (5) | 2, 4 | 4.2, 10 | |
| CD8 | 3, 7 | 4 | 4.1, 4.2 | |
| CD11 | | 2 | 2.1, 4.2 | |

DP "MAS" is provisional designation for a newly defined DP specificity related to the DPB4.2 allele. "CD" cell lines actually are samples from CD patients.
\* — refers to cells with unusual DPw phenotypes.

As shown from the foregoing, the DNA analysis of the HLA DP subtypes shows that specific sequences correlate with the known PLT-defined DPw typings, indicating that the polymorphic epitopes recognized by the primed T cells are on the DPbeta chain. For some DP types, e.g., DPw2 and DPw4, sequence analysis has revealed subtype variants. The variants for DPw2 have been designated DPB2.1 and DPB2.2; cells typed for PLT as DPw4 "new" (e.g., LB1) or DPw4* (e.g., APD) contain the more rare DPB4.2 subtype. The DPB4.2 subtype is more related by sequence to the DPB2.1 allele than to the DPB4.1 allele. Individual CD11 is PLT typed as DPw2, but contains the closely related DPB2.1 and DPB4.2 alleles.

The results above also show that unique DPbeta sequences correspond to the DPw1, DPw3, DPw5, and DPw6 specificities, and these alleles have been designated to reflect this correlation. A few exceptions are, however, that cell line DKY has been typed as DPw5, but contains the DPB2.1 allele, and that individual CD2 is PLT typed as DPw2, but contains the DPB4.2 and DPB10 alleles.

EXAMPLE 2

PCR Amplification of the DPalpha and DPbeta Genes

The DPalpha and DPbeta genes of some of the cells described in Example 1 were amplified by PCR. The primers used, which were synthetic, are shown below. In this depiction, the left side primers, GH98 and DB01, are from the upper strand, and direct DNA polymerase to extend rightward. The right side primers, GH99 and DB03, are from the lower strand, and direct synthesis leftward. The areas of the genes to which the primers bind, and which will act as templates for primer extension are also shown. Lower case letters indicate bases in the primer that are not complementary to the target genomic DNA (shown in the opposite strand). These changes in the primers incorporate restriction enzyme sites (BamHI or pstI) at the ends of the amplified DNA and facilitate cloning of the amplified DNA. The oligonucleotide primers GH98 and GH99, which are used for the amplification of the second exon of DPalpha, amplify a 243 bp segment. The first two bp of the PCR product are from the intervening sequence which flanks the exon. The oligonucleotide primers DB01 and DB03 amplify a 294 bp segment of the second exon of DPbeta. The left 13 bp and the fight 17 bp of the product are from the intervening sequence.

```
                                    DPalpha Primers
                                         15
---------- GH98 ---------->   Phe Val Gln Thr His Arg Pro Thr  .......
c GCGGAt Cc TGTGTCAACTTATGCCGCG TTT GTA CAG ACG CAT AGA CCA ACA  .......
TCGCCTGGTACACAGTTGAATACGGCGC    AAA CAT GTC TGC TGC TCT GGT TGT  .......

70
                              Leu Asn Asn Asn Leu Asn Thr Leu Ile
                              TTG AAC AAC AAC TTG AAT ACC TTG ATC CAGCGTTCCAACCACACTCAGGCCAC
                              AAC TTG TTG TTG AAC TTA TGG AAC TAG GTCGCAAGGTTGGTGTGAc g t CGGTc
                                                                 <-------- GH99 ---------

DPbeta Primers
                                  10                      15
------- DB01 ------->  Leu Phe Gln Gly Arg Gln Glu Cys Tyr  .......
Ca g g g a t CCGCAGAGAATTAC  CTT TTC CAG GGA CGG CAG GAA TGC TAC  .......
GGGGAGGGGCGTCTCTTAATG       GAA AAG GTC CCT GCC GTC CTT ACG ATG  .......

85                 90
                              Glu Leu Gly Gly Pro Met Thr Leu Gln
                              GAG CTG GGC GGG CCC ATG ACC CTG CAG CGCCGAGGTGAGTGAGGGCTTTGG
                              CTC GAC CCG CCC GGG TAC TGG GAC GTC GCGGCTCCACTCACTg a CGt c c t g
                                                                 <-------- DB03 ---------
```

Hybridization of the primers and the synthesis of the elongated primer containing products were essentially as described in EP 258,017 and in the protocols provided by the manufacturer, PECI, of the Thermal Cycler used to perform the PCR. Amplification was for 28 cycles; however, more, i.e., 35, cycles can on occassion yield better results.

Two other illustrative primers of the invention for amplifying the second exon of DPbeta alleles are designated UG19 and UG21. The sequences of these primers and the other illustrative DPbeta primers of the invention are shown below.

| DPbeta Primers | | |
|---|---|---|
| Designation | Sequence | Side |
| DB01 | CAGGGATCCGCAGAGAATTAC | Left |
| DB03 | GTCCTGCAGTCACTCACCTCGGCG | Right |
| UG19 | GCTGCAGGAGAGTGGCGCCTCCGC-TCAT | Left |
| UG21 | CGGATCCGGCCCAAAGCCCTCACTC | Right |

EXAMPLE 3

SSO Probes for Hybridization Analysis of DPbeta Alleles

Illustrative probes of the invention referred to throughout the remainder of the Examples are described below in tabular form. In the Table, the probe designation, probe sequence, polymorphic amino acid sequence encoded in the region of the allele to which the probe hybridizes, segment designation, and hybridization and wash conditions are shown. Probes are shown as having a $^{32}$P or "X" label, where X represents HRP, as discussed in the Examples below. Where a probe sequence is indicated by an X followed by a probe designation, the sequence of the probe is identical to that of the probe designated after the X, except that the $^{32}$P label has been replaced by an HRP label.

Those of skill in the art recognize that depending on the type of label used, hybridization and wash conditions will differ. Although, in a preferred embodiment, the probes will be labeled nonisotopically (e.g., with HRP), some of the probes have been used with isotopic (e.g., $^{32}$P) labels. Consequently, hybridization and wash conditions for $^{32}$P-labeled and HRP-labeled probes are shown, where such conditions have been empirically determined (see Bugawan et al., 1988, *J. Immunol.* 141 (12):4024–4030, incorporated herein by reference). In the Table, the conditions referred to assume a hybridization solution composed of 5×Denhardt's solution, 0.5% SDS, and the indicated amounts (i.e., 0.1×, 3×, 5×) of SSPE. Five×Denhardt's solution contains 0.5 g Ficoll, 0.5 g polyvinylpyrrolidone, 0.5 g BSA (Pentax Fraction V) per 500 ml. The wash solution contains 0.1×SSPE and 0.1% SDS (for HRP-labeled probes, 0.1% Triton X-100 was used in place of SDS); the wash step is carried out at the indicated temperature for ten minutes. As described in Example 11, however, the use of tetramethyl ammonium chloride, or similar salts, can be used to allow for more uniform hybridization and wash conditions, a preferred condition when a number of probes are used in a panel to determine the types of DP alleles in a sample.

SSOs for HLA DPbeta Typing

| Probe Designation | Amino Acid Sequence | Probe Sequence | Region | Hybridiz'n/Wash Conditions |
|---|---|---|---|---|
| DB10 | LFQG | $^{32}$P-GAATTACCTTTTCCAGGGA | A | 5× @ 50°/42° H$_2$O bath |
| DB27 | LFQG | X-DB10 | A | 5× @ 50°/42° air |
| DB11 | VYQL | $^{32}$P-ATTACGTGTACCAGTTACG | A | 3× @ 55°/42° H$_2$O bath |
| DB28 | VYQL | X-DB11 | A | 3× @ 55°/42° H$_2$O bath |
| DB58 | VYQL | X-ATTACGTGTACCAGTTA | A | 3–5× @ 42°/42° air |
| DB23 | VYQL | X-CGTAACTGGTACACGTAAT | A | 5× @ 50°/42° H$_2$O bath |
| DB36 | VYQL | X-DB23 | A | 5× @ 50°/42° air |
| DB12 | VYQG | $^{32}$P-CGTCCCTGGTACACGTAAT | A | 5× @ 50°/42° H$_2$O bath |
| DB29 | VYQG | X-DB12 | A | 5× @ 50°/42° H$_2$O bath |
| DB22 | VHQL | $^{32}$P-ATTACGTGCACCAGTTACG | A | 3× @ 55°/42° H$_2$O bath |
| DB35 | VHQL | X-DB22 | A | 3× @ 50°/42° H$_2$O bath |
| DB13 | AAE | $^{32}$P-CCTGCTGCGGAGTACTG | C | 3× @ 55°/42° H$_2$O bath |
| DB30 | AAE | X-DB13 | C | 3× @ 50°/42° H$_2$O bath |
| DB14 | DEE | $^{32}$P-CAGTACTCCTCATCAGG | C | 5× @ 42°/42° H$_2$O bath |
| DB31 | DEE | X-DB14 | C | 5× @ 42°/42° H$_2$O bath |
| DB16 | EAE | $^{32}$P-CAGTACTCCGCCTCAGG | C | 5× @ 42°/42° H$_2$O bath |
| DB32 | EAE | X-DB16 | C | 3–5× @ 42°/42° H$_2$O bath |
| DB59 | EAE | X-CCTGAGGCGGAGTACTG | C | 5× @ 50°/42° H$_2$O bath |
| DB17 | DED | $^{32}$P-CCTGATGAGGACTACTG | C | 5× @ 50°/42° H$_2$O bath |
| DB33 | DED | X-DB17 | C | 5× @ 50°/42° air |
| DB18 | I-K | $^{32}$P-GACATCCTGGAGGAGAAGC | D | 0.1× @ 55°/42° H$_2$O bath |
| DB34 | I-K | X-DB18 | D | 3× @ 55°/42° H$_2$O bath |
| DB19 | I-E | $^{32}$P-GCTCCTCCTCCAGGATGTC | D | 5× @ 50°/42° H$_2$O bath |
| DB37 | I-E | X-DB19 | D | 5× @ 55°/42° H$_2$O bath |
| DB20 | L-K | $^{32}$P-GACCTCCTGGAGGAGAAGC | D | 3× @ 55°/42° H$_2$O bath |
| DB38 | L-K | X-DB20 | D | 5× @ 55°/42° H$_2$O bath |
| DB21 | L-E | $^{32}$P-GCTCCTCCTCCAGGAGGTC | D | 5× @ 50°/42° H$_2$O bath |
| DB39 | L-E | X-DB21 | | 5× @ 50°/42° air |
| DB62 | L-E | X-GACCTCCTGGAGGAGGAG | D | 3× @ 50°/42° H$_2$O bath |
| DB63 | L-R | X-GACCTCCTGGAGGAGAGG | D | 3× @ 50°/42° H$_2$O bath |
| DB25 | GGPM | $^{32}$P-CTGCAGGGTCATGGGCCCCCG | F | 5× @ 50°/42° H$_2$O bath |
| DB40 | GGPM | X-DB25 | F | 3× @ 50°/42° H$_2$O bath |
| DB26 | DEAV | $^{32}$P-CTGCAGGGTCACGGCCTCGTC | F | 5× @ 50°/42° H$_2$O bath |
| DB41 | DEAV | X-DB26 | F | 3× @ 50°/42° H$_2$O bath |

With reference to the Table above, one should note that because DB28 cross-hybridizes with DB32, superior results can be obtained using probes DB58 and DB59 in place of DB28 and DB32, respectively. In addition, probe DB63 is preferred over DB39.

Example 4

SSO Probes for Hybridization Analysis of DPalpha Alleles

Examples of suitable SSO probes for hybridization analysis of DPalpha alleles are shown below. Two sets of probes are illustrated; each set is designed to distinguish between the polymorphisms in a specific segment of the second exon of the HLA DPalpha gene. ASO1 and ASO2 bind to the DPA1 allele at the region containing the polymorphic segments containing methionine (M) and glutamine (Q), respectively. ASO3 and ASO4 bind to the DPA2 allele to the region containing the polymorphic segments which contain glutamine and arginine (R), respectively. ASO2 and ASO4 distinguish the polymorphic segment containing glutamine from that containing arginine. The probes span the regions encoding these polymorphic amino acid residues. Hybridization using these probes is usually carried out in a solution containing 5×SSPE, 5×Denhardt's, and 0.5% SDS, for at least 1 hour at 42° C. Also shown are the washing conditions for use with the probes.

| HLA DPalpha SSO Probes | | |
|---|---|---|
| Probe | Sequence | Washing Conditions |
| ASO1 | AGATGAGATGTTCTATG | 2 × SSPE, 0.1% SDS, 42° |
| ASO2 | GTTTGGCCAAGCCTTTT | 2 × SSPE, 0.1% SDS, 50° |
| ASO3 | AGATGAGCAGTTCTATG | 2 × SSPE, 0.1% SDS, 50° |
| ASO4 | GTTTGGCCGAGCCTTTT | 2 × SSPE, 0.1% SDS, 55° |

EXAMPLE 5

Analysis of Amplified DPbeta Sequences by Hybridization with SSO Probes

PCR amplified DPbeta sequences from 24 HTCs were analyzed in a dot blot format with a panel (n=9) of $^{32}$P-labeled SSO probes, and the DP type was inferred from the pattern of probe binding. The extraction of DNA from the cells was as described in Example 1. The target regions of the cellular genome, i.e., the second exon of the DPbeta genes, were amplified by the PCR technique as described in Example 2, except that the DNA was from the cells listed in tabular form above.

The amplified DNAs were dot blotted onto a filter; a separate filter containing the panel of samples was prepared for analysis by hybridization with each SSO probe. To dot blot the samples, five microliters of each amplified sample were diluted with 195 microliters of a solution containing 0.4N NaOH and 25 mM EDTA and spotted onto 9 replicate Genatran 45 (Plasco) nylon filters by first wetting the filters with water, placing them in a Bio-dot (Bio-Rad, Richmond, Calif.) apparatus for preparing dot blots, applying the samples, and rinsing each well with 0.4 ml of 20×SSPE (3.6M NaCl, 200 mM $NaH_2PO_4$, and 20 mM EDTA). The filters were removed, rinsed in 2×SSPE, and baked for 30 minutes at 80° C. in a vacuum oven.

The samples on the filters were hybridized with SSO probes of the invention. Hybridization was with 0.25 to 0.5 pmoles of probe in 2 to 5 ml of hybridization solution. Hybridization and wash conditions were as described in tabular form in Example 3. The results of this DPbeta typing are shown below, which also shows the probe with which the samples on the filter were hybridized and the encoded amino acid sequence detected by the probe.

| | | | DPbeta Oligonucleotide Probes | | | | | | | | | |
|---|---|---|---|---|---|---|---|---|---|---|---|---|
| | | | A | | | C | | | D | | | |
| CELL LINE | HLA DR | HLA DPw | DP10 LFQG 4, 2, 5, 7, 8 | DB11 VYQL 6, 3, 11 | DB12 VYQG 1 | DB13 AAE 4.1, 7, 1, 11 | DB14 DEE 4.2, 8, 2.1, 10 | DB17 DED 6, 3, 9, 12 | DB18 I-K 4, 5, 7, 1 | DB19 I-E 2, 8, 9, 10, 12 | DB20 L-K 3 | DPbeta Allele type |
| *1 COX | 3 | 3 | − | + | − | − | − | + | − | − | + | 3 |
| 2 950 | 3 | 1 | − | − | + | + | − | − | + | − | − | 1 |
| *3 BM21 | 11 | blank | − | +/−$^c$ | − | − | + | − | − | + | − | 10 |
| 4 BM16 | 12 | 2 | + | − | − | − | + | − | − | + | − | 2.1 (or 8) |
| 5 BR1G | | 2 | + | − | − | − | + | − | + | + | − | 2.1/4.2 or 4.2/8 |
| 6 JVM | 5 | 2 | + | − | − | − | + | − | − | + | − | 2.1 (or 8) |
| 7 WT46 | 6 | 2 | + | − | − | − | + | − | − | + | − | 2.1 (or 8) |
| 8 MANN | 7 | 2 | + | − | − | − | + | − | − | + | − | 2.1 (or 8) |
| 9 J640 | 4 | 3 | − | + | − | − | − | + | − | − | + | 3 |
| 10 SLE | 13 | 3 | − | + | − | − | − | + | − | − | + | 3 |
| 11 JMF | 7 | 4 | − | + | − | − | − | + | − | − | + | 3 |
| 12 BGE | 2 | 4 | + | − | − | + | − | − | + | − | − | 4.1 (or 7) |
| 13 BM14 | 4 | 4 | + | − | − | + | − | − | + | − | − | 4.1 (or 7) |
| 14 BM92 | 4 | 4 | + | −/+$^d$ | − | − | + | − | + | − | − | 4.2 |
| 15 TS10 | 4 | 4 | + | − | − | + | − | − | + | − | − | 4.1 (or 7) |
| 16 RLO | 4 | 4 | + | − | − | + | − | − | + | − | − | 4.1 (or 7) |
| *17 APD | 6 | 4 | + | − | − | − | + | − | + | − | − | 4.2 |
| 18 BUP | 7 | 4 | + | − | − | + | + | − | + | − | − | 4.1/4.2 |
| 19 MMR | | 4 | + | − | − | + | − | − | + | − | − | 4.1 (or 7) |
| *20 LUY | 8 | 4/1 | + | − | + | + | − | − | + | − | − | 1/4.1 (or 7) |
| 21 YOS | 4 | 4 | + | − | − | − | + | − | + | −/+$^d$ | − | 4.2 |
| *22 DKY | 9 | 5 | + | − | − | − | + | − | − | + | − | 2.1 (or 8) |
| 23 HAS | 4 | 5 | + | − | − | − | − | − | + | −/+$^d$ | − | 5 |
| *24 TOK | 2 | blank | − | −/+$^c$ | − | − | − | + | − | + | − | 9 |

*Cell line DPbeta type confirmed by DNA sequencing. +/− designates weak signal. Superscript c indicates the presence of an additional polymorphic sequence in region A encoding the residues VHYL, which cross-hybridizes with the DB11 probe (no cross-hybridization occurs with probe DB22). Superscript d represents cross-hybridizing due to the ability of the DB11 probe to bind to sequences recognized by the DB10 probe (cell line BM92) or due to the ability of the DB19 probe to bind to sequences recognized by the DB18 probe (cell lines YOS and HAS).

The determination of DPbeta types of the cells based upon the hybridization analysis with the SSO probes has been discussed above. To determine the DPbeta type of a sample, the binding of the probes to the sample was examined. The alleles present were inferred from the pattern of probe binding. For example, sample 1 formed hybrids with SSO probes DB11, DB17, and DB20. The amino acids encoded by DB11, DB17, and DB20 are VYQL, DED, and LEEK, respectively. An examination of segments A, C, and D of the DPbeta allelic amino acid sequences shows that the sequence VYQL is present in DPB6, DPB11, and DPB13; the sequence DED is present in DPB17, DPB14, DPB12, DPB9, DPB6, and DPB3; the sequence LEEK (L__K) is present in DPB18, DPB14, DPB4.1, DPB4.2, DPB5, DPB7, DPB3, and DPB1. The only allele which contains the three sequences which hybridize with the probe is DPB3. Thus, the DP type of sample 1 based on SSO typing is DPB3.

The DPB types of the other samples were inferred by the same type of analysis, and the determined types are depicted above. In the depiction, the asterisk (*) indicates cells where the DPw genotype was also determined by sequence analysis. The DPbeta type of the cell lines COX (formerly w1→w3) and BM21 (formerly w1→ blank) have recently been changed to the type indicated. The symbol ± refers to a weak signal obtained with a probe. In some cases (BM21 and TOK), this weak signal reflects the presence of an additional polymorphic sequence in region A encoding the amino acid residues VHYL, which cross-hybridizes to the DB11 probe. The sequence can be more conveniently typed with region A probe DB22. For other cell lines (BM92), there is apparently a background cross-hybridization of the DB11 probe to the sequences recognized by the DB10 probe. In similar fashion, cross-hybridization signals can occur with the DB19 probe on sequences complementary to the DB18 probe.

The panel of SSO used in this Example detects variation at only 3 of the 5 polymorphic regions and does not detect all allelic variants at these 3 regions. The typing system using the procedure of this example is simple and unequivocal for HTCs, but given the patchwork pattern of polymorphism, can occasionally give rise to ambiguous typing for heterozygous individuals if the hybridization pattern of the various probes can be interpreted as more than a unique pair of alleles. This ambiguity arises from the many different combinations of the DPbeta sequence variants that constitute the different DPbeta alleles. However, with the use of the additional SSO probes provided by the invention, which additional probes span the remaining polymorphic regions, unambiguous typings can be obtained for heterozygous individuals.

EXAMPLE 6

HLA DP Typing of Coeliac Disease Patients by DNA Sequence Analysis of PCR Amplified Target Regions The cells of four patients with coeliac disease (CD) were PLT-typed, and the DNA sequences of the second exon of the DPbeta determined as described in Example 1. The CD diagnosis was based on clinical symptomology.

The results of the analysis obtained by DNA sequencing of the DPbeta (second exon) of the CD cells has been discussed above. From these results, one observes that, when CD cells are compared to non-CD cells, there is an apparent increase in the frequency of the DPB4.2 allele. In addition, the DPB10 allele sequence is present in two independent CD patients yet observed in only one of the 30 non-CD cell lines.

EXAMPLE 7

HLA DP Typing of Coeliac Disease Patients by SSO Probe Hybridization Analysis

The cells of 19 patients with CD and of 43 non-CD controls were analyzed for HLA DP type by SSO probe hybridization analysis. The diagnosis of CD was based on clinical symptomology; the CD patients as well as control individuals were all from Italy. DNA extraction was as described in Example 1. PCR amplification of the samples was as described in Example 2. Analysis of the amplified sequences was as described in Example 4.

The results of the analysis showed that there was a significant increase in the DPB4.2 allele in CD patients as compared to non-CD controls; this allele was present in 12 of 19 CD patients, but only 3 of 43 control patients. The DPB4.2 and DPB3 alleles were present in 17 of. 19 CD patients and in 15 of 43 controls. The genotype DPB4.1/4.2 was present in 10 of 19 CD patients and in only 1 of 43 controls.

EXAMPLE 8

HLA DP Typing of Forensic Samples

Samples which contain genomic nucleic acids of the suspect individual are obtained. The target regions of the genome, i.e., the regions containing the second exon of the DPalpha and DPbeta genes, are amplified by the PCR technique, as described in Example 2, except that the nucleic acids from the suspect replace those of the cells in the Example, and except that the amplified samples contain a 32P-label. The amplified sample is hybridized with the probes of the invention, which have been dot blotted onto the same filter, and which have been immobilized on the filter by poly-dT tails. The techniques for preparing the immobilized sequence-specific probes are described in U.S. Ser. No. 197,000, filed May 20, 1988, in Ser. No. 347,495, filed May 4, 1989, and in PCT Patent Publication No. WO 89/11548. The hybridization and washing conditions for the filter allow only perfectly matched hybrids to remain in duplex state. The filters are examined to determine which probes form hybrids with the labeled sample.

A sample which is to be compared with that obtained from the suspect is examined for DP type by the same procedure, i.e., by PCR amplification and hybridization with immobilized SSO probes. The pattern of binding to the SSO probes of the sample from the suspect and of the comparison sample is examined to determine the similarity or difference in the hybridization patterns.

EXAMPLE 9

HLA DP Typing Using SSO Probes

Labeled with Horseradish Peroxidase

A panel of cells from 39 individuals was typed for DPbeta alleles using SSO probes for the second exon variants. The probes were labeled with horseradish peroxidase (HRP), and hybrids detected in a dot blot format.

The cells analyzed were from fourteen IDDM patients, five DR3 control non-IDDM patients, and nineteen HTCs which typed by PLT as DP blank. IDDM patients were identified by clinical symptomology. DNA was isolated from the cells as described in Example 1. The target region, i.e., the second exon of the DPbeta alleles, was amplified using the PCR technique in 200 microliters of reaction mixture that contained 50 mM Tris-HCl, pH 8.3; 2.5 mM $MgCl_2$; 100 micrograms/ml gelatin; 0.75 mM in each of the four deoxynucleoside triphosphates; the primers DB01 and DB03; and Taq polymerase. The ramping for amplification was the following: heating for 30 seconds to 94° C. followed by incubation at that temperature for 30 seconds; cooling for 1 minute to 55° C. followed by incubation at that temperature for 30 seconds; heating to 72° C. for 30 seconds followed by incubation at that temperature for 45 seconds. This cycling was repeated for 42 cycles. After amplification, the reaction mixtures were sampled and monitored by gel electrophoresis on gels containing 3% Nusieve, 1% Agarose to determine if all the DNA amounts were comparable.

Filters containing the dot blotted samples were prepared by blotting 150 microliters/dot of denatured amplified DNA on Genatran nylon membranes and UV treating the filters containing the samples for 5 minutes. The latter treatment is to fix the sample to the membranes. The amplified DNAs were denatured by treating 5 microliters of the PCR reaction mixture in a total volume of 150 microliters containing 0.4N NaOH and 25 mM EDTA. Eight replicate filters were prepared for hybridization with HRP labeled ASO probes.

Prior to hybridization, the sample containing filters were incubated for 15 minutes in pre-hybridization solution (1×SSPE, 5×Denhardt's solution, 1% Triton X-100) without probe. In the pre-hybridization solution, Triton X-100 was used in place of SDS. Hybridization was done in the same solution, which additionally contained 1 picomole probe/ml. Each filter was incubated for 40 minutes with 2.5 ml of hybridization solution containing one of the HRP labeled probes. The probes used were DB27, DB28, DB29, DB30, DB31, DB32, DB33, and DB35. The probes and hybridization conditions are listed in tabular form in Example 3. After hybridization, the filters were washed as stated in Example 3, under suitably stringent conditions, i.e., in 0.1×SSPE, 0.1% Triton X-100 for 5 minutes at 42° C. The HRP-labeled SSO probes were prepared essentially by the methods disclosed in abandoned application U.S. Ser. No. 103,978 and U.S. Pat. No. 4,914,210, both filed 2 Oct. 1987, and incorporated herein by reference.

These methods essentially involve derivatizing the nucleic acid probe using a linear linking molecule comprising a hydrophilic polymer chain (e.g., polyoxyethylene) having a phosphoramidite moiety at one end and a protected or unprotected sulfhydryl moiety at the other end. The phosphoramidite moiety couples to the nucleic acid probe by reactions well known in the art (e.g., Beaucage et al., 1988, *Tetrahedron Lett.* 22:1859–1862), while the sulfhydryl group is free to form disulfide or other covalent bonds with the protein, e.g., HRP. In Ser. No. 103,978, the HRP is conjugated to the linking molecule through an N-maleimido-6-aminocaproyl group. The label is prepared by esterifying N-maleimido-6-aminocaproic acid with sodium 4-hydroxy-3-nitrobenzene sulfonate in the presence of one equivalent of dicyclohexylcarbodiimide in dimethylformamide. After purification, the product is added to phosphate buffer containing HRP at a ratio of 1:8 HRP to ester. The oligonucleotide probe is synthesized in a DNA synthesizer, and the linking molecule having the structure $(C_6H_5)_3CS-(CH_2CH_2O)_4-P(CH_2CH_2CN)[N(i-PR)_2]$ attached using phosphoramidite synthesis conditions. The trityl group is removed, and the HRP derivative and probe derivative are mixed together and allowed to react to form the labeled probe. A biotin-labeled probe or primer may be prepared by similar methods.

Samples which contained hybridized probe were detected using a color development reaction, as described in Sheldon et al., 1986 *Proc. Natl. Acad. Sci. U.S.A.* 83:9085–9089, which utilizes $TMB/H_2O_2$. The detection system is described in copending U.S. Ser. No. 197,000, filed May 20, 1988, in Ser. No. 347,495, filed May 4, 1989, and in PCT Patent Publication No. WO 89/11548. and in Example 10 below. The HLA DP genotypes of the amplified DNA samples were readily apparent from the filters.

EXAMPLE 10

HLA DPbeta Typing with HRP Labeled SSO Probes

A. PCR Amplification

DPB typing can utilize as many as or more than 14 SSO probes (sequence specific oligonucleotides), so amplification is carried out on 0.5 to two micrograms of DNA, in 200 microliters of reaction volume, if DNA is not limiting. Lower amounts of DNA, i.e., 100 ng, can be amplified, but more cycles of amplification should be performed with such samples, i.e., 45 cycles.

The PCR reaction is started by mixing the following by vortexing for 1 to 2 seconds.

| | |
|---|---|
| DNA | 0.5 to 2 µg |
| 10 × Taq buffer | 20 µl |
| 100 mM dNTPs | 1.5 µl |
| DPB primer [10 µM UG19 or DB01] | 10 µl |
| DPB primer [10 µM UG21 or DB03] | 10 µl |
| Taq polymerase 5 U/µl | 1.2 µl |

Glass-distilled $H_2O$ is added to achieve a final volume of 200 µl. 10×Taq salts are 500 mM KCl; 100 mM Tris, pH 8.3; 15 mM $MgCl_2$; and 1 mg/ml gelatin. Negative controls (i.e., no DNA) should be included in each PCR run. Typically, 30–35 cycles of amplification in a Perkin-Elmer/Cetus Instruments DNA Thermal Cycler are sufficient. The cycles are designed to denature at 96° C. for 30 seconds, and anneal and extend at 65° C. for 30 seconds. If primer pair DB01/DB03 is used, annealing is at 55° C. for 30 seconds and extending is at 72° C. for 30 seconds. Analytical gels can be used to check PCRs and to quantitate amount of DNA to be used for dot-blots.

B. Dot blot

Typically, 5 µl of the amplified DNA contain approximately 200 ng, more than enough for a single dot blot. Remember, however, that as many as or more than 14 dots may be required, i.e., about 70 µl of the amplification reaction would then be used in preparing the dot blots. For each 5 µl of amplification reaction, 50 µl of 0.4N NaOH and 25 mM EDTA are added to the DNA. Five minutes is sufficient to complete denaturation of DNA. The Genatran membrane is first wetted in 2×SSPE, and then the 150 µl of denatured DNA are loaded into the dot blot apparatus. The membrane is rinsed in 2×SSPE, and the DNA is fixed to the membrane with exposure to UV light for five minutes, i.e., by a 55 $mJ/cm^2$ exposure in a Stratalinker 1800™ UV light box, marketed by Stratagene.

C. Hybridization

The membrane is again wetted in 2×SSPE, and about 5 ml of hybridization solution per 8×12 cm membrane (size of dot blot apparatus) are added. About 1 to 1.5 picomoles of HRP probe are added per ml hybridization solution, and the probes are allowed to hybridize for at least one hour. Hybridization solution is SSPE (as indicated above), 5×Denhardt's, and 1% Triton X-100. The membranes are then washed with 0.1 × SSPE and 0.2% Triton X-100 for ten minutes. Otherwise, hybridization and wash conditions were as described in Example 3. The probes used were DB27, DB29, DB30, DB31, DB33, DB34, DB35, DB37, DB38, DB40, DB41, DB58, DB59, DB62, and DB63.

D. Detection

The following steps for detection of probes are done at room temperature with moderate shaking and just enough solution to cover the membrane, completely, as is described in Bugawan et al., 1988, *BiO/Technology* 6:943–947, incorporated herein by reference. The detection is carried out by a 5 minute incubation of the membrane with Buffer B, a 5 minute wash with Buffer C, and 10 minutes incubation under light exclusion with Buffer C and TMB (48 ml of Buffer C and 2.5 ml of 2 mg/ml TMB). Buffer B is 100 mM NaCl, 1M urea, 5% Triton X-100, and 1% dextran sulfate. Buffer C is 100 mM sodium citrate, pH 5.0. TMB is 3, 3', 5, 5'-tetramethylbenzidine. About 23 μl of 3% $H_2O_2$ are added to 50.5 ml of Buffer C/TMB; the resulting solution is used to develop the color on the membranes (color comes up within 1–5 minutes) under light-excluding conditions. The color development is stopped by washing in $H_2O$ with a small amount of Buffer C. The wash is repeated twice for 30 minutes. Pictures of the membrane are taken and the membrane is stored in Buffer C under no light.

The methods described herein, as well as the SSO probes and primers, and kits containing them, are useful for the accurate, relatively simple, and economic determination of an individual's HLA-DP genotype. Accurate DP typing will prove important in several medical applications. For example, accurate HLA-DP matching of donors and recipients will be helpful in the prevention of allograft rejection and in the prevention of host versus graft disease. Because certain HLA DP genotypes appear to be linked to certain autoimmune diseases, including, for example, coeliac disease, myasthenia gravis, and IDDM, HLA DP DNA typing is useful in an early diagnosis of the disease, prior to manifestation of full clinical symptoms.

Accurate HLA-DP typing is useful in forensic medicine. For example, it provides evidence as to whether a sample which contains genomic nucleic acids, for example, blood, hair, or semen is derived from a suspect individual. It is also useful in determining an individual's paternity or maternity. The latter is of particular importance in analyzing historical samples.

EXAMPLE 11

Probe Hybridization in TMACL

When tetramethyl ammonium chloride (TMACL) is present in a hybridization solution, probe discrimination is based on probe length and not on the G, C, A, or T composition of the probe. Thus, by using TMACL in the hybridization solution, one can hybridize and wash many different probes at a single temperature.

A suitable hybridization solution for this purpose contains 3M TMACL; 0.5% SDS; 10 mM Tris-HCl, pH=7.5; and 0.1 mM EDTA. Hybridizations are carried out at 55° C. for 30 to 60 minutes for 19-mer probes DB27, DB28, DB29, DB35, DB34, DB37, DB38, and DB62; at 50° C. for 17-mer probes DB30, DB31, DB33, and DB59; and at 60° C. for DB40 and DB41. The wash solution is 3M TMACL; 50 mM Tris-HCl, pH=8; and 2 mM EDTA. The wash is carried out first at 37° C. for 20 minutes, then at the higher stringency temperature (the hybridization temperature) for 10 minutes. Detection of hybridization is carried out as described in Example 10.

Additional probes useful for this, or any other, hybridization format for purposes of the present invention are shown below (X is HRP).

| Probe Designation | Sequence | Length | Amino Acid Sequence |
|---|---|---|---|
| DB70 | X-GAATTACCTTTTCCAGGGAC | 20-MER | LFQG |
| DB92 | X-GACCTCCTGGAGGAGGAGC | 19-MER | L-E |
| DB93 | X-GACCTCCTGGAGGAGAGGC | 9-MER | L-R |
| DB94 | X-AGCTGGGCGGGCCCATGAC | 19-MER | GGPM |
| DB95 | X-AGCTGGACGAGGCCGTGAC | 19-MER | DEAV |
| DB64 | X-CTGGTCGGGCCCATGACC | 18-MER | VGPM |
| DB72 | X-ACATCCTGGAGGAGAAGC | 18-MER | I-K |
| DB73 | X-ACATCCTGGAGGAGGAGC | 18-MER | I-E |
| DB74 | X-ACCTCCTGGAGGAGAAGC | 18-MER | L-K |
| DB71 | X-TTACGTGTACCTGGGAC | 17-MER | VYQG |
| DB75 | X-CCTGATGAGGAGTACTG | 17-MER | DEE |
| DB76 | X-CTGGGCGGGCCCATG | 15-MER | GGPM |
| DB77 | X-CTGGACGAGGCCGTG | 15-MER | DEAV |

We claim:

1. A process for determining an individual's HLA DP genotype from a nucleic acid-containing sample obtained from the individual comprising:

(a) amplifying a nucleic acid sequence from exon two of an HLA DPbeta gene in the nucleic acids in the sample, wherein the amplifying comprises treating said sample under conditions suitable for carrying out a polymerase chain reaction;

(b) mixing the amplified nucleic acids with a panel of sequence specific oligonucleotide (SSO) probes; wherein said panel of probes is capable of determining a genotype comprising an allele selected from the group consisting of DPB1, DPB2.2, DPB4.2, DPB5, DPB6, DPB8, DPB9, DPB10, DPB11, DPB13, DPB14, DPB15, DPB16, DPB17, DPB18, DPB19, and DPB20; and wherein each probe consists of a nucleotide sequence complementary to a variant sequence of a variable segment of said HLA DPbeta gene, wherein said variable segment is selected from the group of variable segments consisting of nucleotides coding for amino acid positions 8–11, 36, 55–57, 65–69, 76, and 84–87 of exon two of said HLA DPbeta gene, under conditions wherein said SSO probes bind to said amplified nucleic acids to form stable hybrid duplexes only if said probes and said amplified nucleic acid are exactly complementary;

(c) detecting hybrids formed between the amplified nucleic acid sequence and the SSO probes; and (d) determining said individual's HLA DPbeta genotype from the presence or absence of said hybrids.

2. The process of claim 1, wherein each probe consists of a nucleotide sequence 17 to 23 nucleotides in length which is complementary to a variant sequence of one of said variable segments of said DPbeta gene.

3. The process of claim 1, wherein said polymerase chain reaction is carried out in the presence of a primer selected from the group consisting of DB01, DB03, UG19, and UG21 primers.

4. The process of claim 3, wherein the probes of the panel are selected from the group consisting of:
5'GAATTACCTTTTCCAGGGA; 5'ATTACGTGTACCAGTTACG;
5'ATTACGTGTACCAGTTA; 5'CGTAACTGGTACACGTAAT;
5'CGTCCCTGGTACACGTAAT; 5'ATTACGTGCACCAGTTACG;
5'CCTGCTGCGGAGTACTG; 5'CAGTACTCCTCATCAGG;
5'CAGTACTCCGCCTCAGG; 5'CCTGAGGCGGAGTACTG;
5'CCTGATGAGGACTACTG; 5'GACATCCTGGAGGAGAAGC;
5'GCTCCTCCTCCAGGATGTC; 5'GACCTCCTGGAGGAGAAGC;
5'GCTCCTCCTCCAGGAGGTC; 5'GACCTCCTGGAGGAGGAG;
5'GACCTCCTGGAGGAGAGG;
5'CTGCAGGGTCACGGCCTCGTC; 5'GAATTACCTTTTCCAGGGAC;
5'GACCTCCTGGAGGAGAGC; 5'GACCTCCTGGAGGAGAGGC;
5'AGCTGGGCGGGCCCATGAC; 5'AGCTGGACGAGGCCGTGAC;
5'CTGGTCGGGCCCATGACC; 5'ACATCCTGGAGGAGAAGC;
5'ACATCCTGGAGGAGGAGC; 5'ACCTCCTGGAGGAGAAGC;
5'CCTGATGAGGAGTACTG;
5'CTGGGCGGGCCCATG; and 5'CTGGACGAGGCCGTG.

5. A panel of purified sequence specific oligonucleotide (SSO) probes useful for determining an individual's HLA DP genotype from a nucleic acid containing sample obtained from the individual, wherein said panel of probes is capable of determining a genotype comprising an allele selected from the group consisting of DPB1, DPB2.2, DPB4.2, DPB5, DPB6, DPB8, DPB9, DPB10, DPB11, DPB13, DPB14, DPB15, DPB16, DPB17, DPB18, DPB19, and DPB20; and wherein each of said probes consists of a nucleotide sequence between 17 and 23 nucleotides in length that is totally complementary to a variant sequence of a variable segment of an HLA DPbeta gene, wherein said variable segment selected from the group of variable segments consisting of nucleotides coding for amino acid positions 8–11, 36, 55–57, 65–69, 76 and 84–87 of the second exon of said HLA DPbeta gene.

6. A kit useful for determining an individual's HLA DP genotype comprising
said panel of SSO probes of claim 5.

7. The kit of claim 6 further comprising a container containing oligonucleotide primers useful for amplification of a a second exon sequence of an HLA DPbeta gene.

8. A process for determining if an individual has an HLA DPbeta genotype associated with an autoimmune disease comprising determining the individual's HLA DPbeta genotype according to the process of claim 1 and determining whether the individual's genotype is one which is associated with said autoimmune disease.

9. The process of claim 8, wherein the autoimmune disease is juvenile rheumatoid arthritis, and the genotype which is associated with said autoimmune disease comprises the DPB2.1 allele.

10. The process of claim 8, wherein the autoimmune disease is insulin dependent diabetes mellitus.

11. The process of claim 8, wherein the autoimmune disease is coeliac disease and the genotype which is associated with said autoimmune disease comprises an allele selected from the group consisting of DPB13, DPB1, DPB3, and DPB4.2.

12. A process of providing forensic evidence concerning whether a sample which contains genomic nucleic acids is derived from a suspected individual, wherein said process comprises determining according to the process in claim 1 the HLA DPbeta genotype of the sample and of the suspected individual, and comparing the HLA DPbeta genotypes of the individual and of the sample.

* * * * *